(12) United States Patent
Zhu et al.

(10) Patent No.: US 12,376,832 B2
(45) Date of Patent: Aug. 5, 2025

(54) IMAGE COMPOUNDING FOR MIXED TRANSDUCER ARRAYS

(71) Applicant: DEEPSIGHT TECHNOLOGY, INC., Los Altos, CA (US)

(72) Inventors: Liren Zhu, Sunnyvale, CA (US); Danhua Zhao, San Jose, CA (US)

(73) Assignee: DeepSight Technology, Inc., Santa Clara, CA (US)

( * ) Notice: Subject to any disclaimer, the term of this patent is extended or adjusted under 35 U.S.C. 154(b) by 0 days.

(21) Appl. No.: 18/032,953

(22) PCT Filed: Oct. 21, 2021

(86) PCT No.: PCT/US2021/056096
§ 371 (c)(1),
(2) Date: Apr. 20, 2023

(87) PCT Pub. No.: WO2022/087301
PCT Pub. Date: Apr. 28, 2022

(65) Prior Publication Data
US 2023/0380813 A1  Nov. 30, 2023

Related U.S. Application Data

(60) Provisional application No. 63/104,886, filed on Oct. 23, 2020.

(51) Int. Cl.
*A61B 8/00* (2006.01)
(52) U.S. Cl.
CPC .......... *A61B 8/5261* (2013.01); *A61B 8/4488* (2013.01)

(58) Field of Classification Search
CPC .......................... A61B 8/5261; A61B 8/4488
See application file for complete search history.

(56) References Cited

U.S. PATENT DOCUMENTS 5,908,389 A * 6/1999 Roundhill .............. A61B 8/463
600/443
6,039,690 A * 3/2000 Holley .................... A61B 8/14
600/440

(Continued)

FOREIGN PATENT DOCUMENTS

WO  2016131647 A1  8/2016
WO  2021202093 A1  10/2021
WO  2021237125 A1  11/2021

OTHER PUBLICATIONS

Colin et al.; "Broadband optical ultrasound sensor with a unique open-cavity structure"; Journal of Biomedical Optics 16(1), 017001 (Jan. 2011).*

(Continued)

*Primary Examiner* — Dixomara Vargas
(74) *Attorney, Agent, or Firm* — Kilpatrick Townsend & Stockton LLP

(57) ABSTRACT

A method of imaging may include receiving a first signal from one or more array elements of a first type in a mixed transducer array, receiving a second signal from one or more array elements of a second type in the mixed transducer array where at least one of the first type and the second type is an optical sensor, generating a first image from the first signal and a second image from the second signal, and combining the first image and the second image to generate a compound image.

27 Claims, 14 Drawing Sheets

(56) References Cited

U.S. PATENT DOCUMENTS

| | | | |
|---|---|---|---|
| 9,255,914 B2 * | 2/2016 | Yoshida | G01N 29/0672 |
| 9,274,215 B2 * | 3/2016 | Zhao | G01S 7/523 |
| 9,668,714 B2 * | 6/2017 | Call | G01S 15/8927 |
| 11,620,772 B2 * | 4/2023 | Rosen | G06V 10/764 |
| | | | 600/408 |
| 2004/0064043 A1 * | 4/2004 | Rielly | G01S 15/8954 |
| | | | 600/437 |
| 2007/0149879 A1 * | 6/2007 | Roundhill | A61B 8/08 |
| | | | 600/458 |
| 2008/0146942 A1 | 6/2008 | Dala-Krishna | |
| 2008/0242979 A1 * | 10/2008 | Fisher | A61B 8/4416 |
| | | | 600/427 |
| 2009/0208080 A1 * | 8/2009 | Grau | G06T 5/50 |
| | | | 382/294 |
| 2009/0264760 A1 * | 10/2009 | Lazebnik | A61B 8/08 |
| | | | 382/128 |
| 2010/0172567 A1 * | 7/2010 | Prokoski | A61B 5/418 |
| | | | 348/47 |
| 2010/0231903 A1 | 9/2010 | Sumetsky | |
| 2013/0116538 A1 * | 5/2013 | Herzog | A61B 8/4281 |
| | | | 600/407 |
| 2013/0253325 A1 * | 9/2013 | Call | A61B 8/5246 |
| | | | 600/447 |
| 2013/0338501 A1 * | 12/2013 | Clingman | A61B 5/4312 |
| | | | 600/440 |
| 2014/0012124 A1 * | 1/2014 | Zalev | A61B 5/0095 |
| | | | 600/407 |
| 2014/0093150 A1 * | 4/2014 | Zalev | A61B 5/726 |
| | | | 382/128 |
| 2014/0254307 A1 * | 9/2014 | Zhao | G01S 15/8906 |
| | | | 367/7 |
| 2015/0075287 A1 * | 3/2015 | Herzog | G01H 9/004 |
| | | | 73/655 |
| 2015/0313576 A1 * | 11/2015 | Yamamoto | A61B 8/5246 |
| | | | 600/447 |
| 2016/0019702 A1 * | 1/2016 | Park | G01S 7/52038 |
| | | | 382/131 |
| 2016/0128675 A1 * | 5/2016 | Kang | A61B 8/463 |
| | | | 600/443 |
| 2017/0112577 A1 * | 4/2017 | Bonutti | A61B 34/20 |
| 2017/0322071 A1 * | 11/2017 | Schmid | A61B 5/7203 |
| 2018/0000452 A1 * | 1/2018 | Adams | G01S 7/52095 |
| 2019/0076130 A1 | 3/2019 | Bhuyan et al. | |
| 2019/0213761 A1 * | 7/2019 | Rosen | A61B 8/463 |
| 2019/0320878 A1 * | 10/2019 | Duindam | G06T 7/30 |
| 2020/0342593 A1 * | 10/2020 | Honjo | A61B 8/5207 |
| 2021/0015460 A1 * | 1/2021 | Miyachi | G01S 15/8995 |
| 2021/0019488 A1 * | 1/2021 | Chau | G06V 40/1329 |

OTHER PUBLICATIONS

Sahar et al.; "Precision ultrasound sensing on a chip"; Nature Communications | (2019) 10:132 |.*

Himanshu et al.; "Combining Subharmonic and Ultraharmonic Modes for Intravascular Ultrasound Imaging: A Preliminary Evaluation"; Ultrasound in Medicine & Biology vol. 43, Issue 11 , Nov. 2017, pp. 2725-2732.*

Monifi, et al., "Ultrasound Sensing Using a Fiber Coupled Silica Microtoroid Resonator Encapsulated in a Polymer", 2013 IEEE Photonics Conference, Bellevue, WA, USA, doi: 10.1109/IPCon.2013.6656511, 2013, pp. 2015-2016.

Wei, et al., "High-Frequency Ultrasonic Sensor Arrays Based on Optical Micro-ring Resonators", Proc. SPIE 10600, Health Monitoring of Structural and Biological Systems XII, 1060003, Mar. 27, 2018, 8 pages.

PCT App. No. PCT/US2021/056096, "International Preliminary Report on Patentability", May 4, 2023, 10 pages.

US International Search Report and Written Opinion for PCT/US2021/05696 mailed Jan. 25, 2022.

EP21883922.3 , "Extended European Search Report", Aug. 30, 2024, 11 pages.

* cited by examiner

Spectra of Optical Resonator Signals and Filters

Broad Bandwidth Optical Resonator Signals

IMAGE COMPOUNDING FOR MIXED TRANSDUCER ARRAYS

CROSS-REFERENCE TO RELATED APPLICATIONS

This application claims priority to U.S. patent application Ser. No. 63/104,886 filed on Oct. 23, 2020, which is incorporated herein in its entirety by this reference.

TECHNICAL FIELD

The present disclosure generally relates to the field of imaging, and in particular to methods and devices that enable forming a compound image from images acquired by a mixed array including an array of optical sensors and other transducers. The methods and devices disclosed herein include optical sensors that have high sensitivity and/or high operational bandwidth for improved imaging performance.

BACKGROUND

Ultrasound sensing is used in various industries including medical imaging and medical diagnosis due to a number of advantages. For example, ultrasound sensing utilizes ultrasound signal which has a remarkable penetration depth. Moreover, ultrasound imaging is known to be an advantageously non-invasive form of imaging, as it is based on non-ionizing radiation.

Various known ultrasound transducers used in ultrasound imaging have numerous drawbacks. For example, some ultrasound transducers are made of piezoelectric material, such as lead zirconate titanate (PZT). However, the 6-dB bandwidth of PZT materials is generally limited to only about 70%. Certain composite PZT materials have a slightly increased bandwidth, but still only achieve a bandwidth of up to about 80%. As another example, single crystal materials have increasingly been used in an effort to improve performance of ultrasound probes but have lower Curie temperatures and are brittle. Another type of transducer material is silicon, which can be processed to build Capacitive Micromachined Ultrasound Transducer (CMUT) probes that can have increased bandwidth. However, CMUT probes are not very sensitive or reliable. Moreover, CMUT probes have several operational limitations. For example, CMUT probes are nonlinear sensors and, therefore, are not generally suitable for harmonic imaging. Thus, there is a need for ultrasound probes with mixed transducer arrays (mixed arrays) that include sensors with higher bandwidth and sensitivity. Moreover, there is a need for back end devices, and/or front end devices to process signals and/or images generated by the mixed arrays.

SUMMARY

Generally, in some variations, an apparatus (e.g., an image compounding system) for imaging (e.g., ultrasound imaging a patient) may include a mixed transducer array including one or more array elements of a first type configured to receive a first signal, and one or more array elements of a second type configured to receive a second signal, wherein at least one of the first type and the second type is an optical sensor. The apparatus may further include one or more processors configured to generate a first image from the first signal and a second image from the second signal, and combine the first image and the second image to generate a compound image.

In some variations, the array elements of the first type may include a non-optical transducer and the array elements of the second type may include an optical sensor. The one or more array elements of the first type may include, for example, a piezoelectric transducer, a single crystal material transducer, a piezoelectric micromachined ultrasound transducer (PMUT), or a capacitive micromachined ultrasonic transducer (CMUT). The optical sensor may include, for example, a whispering gallery mode (WGM) optical resonator, a microbubble optical resonator, a photonic integrated circuit (PIC) optical resonator, a microsphere resonator, a microtoroid resonator, a microring resonator, a microbottle resonator, a microcylinder resonator, and/or a microdisk optical resonator.

In some variations, the array elements of the second type may include optical sensors with different characteristics (e.g., different design and/or different operating parameters). For example, in some variations, the array elements of the second type may include one or more high quality factor (high Q) optical sensors, and one or more low quality (low Q) optical sensors. Additionally or alternatively, the array elements of the second type may include one or more tunable optical resonators configured to operate as a high Q optical resonator, and/or the array elements of the second type may include one or more tunable optical resonators configured to operate as a low Q optical resonator. For example, such tunable optical resonators may be selectively operable in a high Q or low Q mode, depending on imaging settings, etc.

Furthermore, in some variations, the mixed transducer array may include a combination of one or more non-optical transducers and multiple types of optical sensors. For example, the mixed transducer array may include one or more array elements of a first type including at least one non-optical transducer, one or more array elements of a second type may include at least one type of optical sensor, and one or more array elements of a third type may include at least another type of optical sensor. The one or more processors may be further configured to generate a third image from the third signal, and combine the first image, the second image, and the third image to generate a compound image. Different types of optical resonator sensors may include, for example, a high Q optical resonator and a low Q optical resonator (or a tunable optical resonator sensor configured to operate as a high Q optical resonator or a low Q optical resonator). As another example, different types of optical resonator sensors may include a broad bandwidth optical resonator and an ultra-sensitive optical resonator.

In some variations, one or more array elements of the mixed transducer array (e.g., transducers) may transmit acoustic signals at a fundamental frequency f. In response, the one or more array elements of the first type, the second type, or both the first type and the second type may produce one or more responses upon receiving harmonic (including super-harmonic and sub-harmonic) acoustic echoes corresponding to the transmitted acoustic signal. The one or more array elements of the second type may have a bandwidth ranging from at least f/M to Nf, where M and N are integers greater than 1. In some variations, the one or more array elements of the first type may transmit acoustic signals at a first fundamental frequency $f_1$ and a second fundamental frequency $f_2$. In response, the one or more array elements of the second type may produce one or more optical responses upon receiving acoustic echoes that correspond to a frequency of one or more linear combinations $nf_1+mf_2$, wherein n and m are integers such that $nf_1+mf_2$ is a positive number. At least one of the first image and the second image may be or include a harmonic image.

In some variations, the one or more processors may be configured to filter the various signals from the different types of array elements in the mixed transducer array, using one or more suitable filters. Such suitable filters may include, for example, a harmonic band-pass filter that may enable extraction of the harmonic signals, including sub-harmonic and super harmonic signals.

Combining the first image and the second image may be performed by a suitable compounding algorithm. For example, the one or more processors may be configured to combine the first and second images at least in part by determining an average of the first image and the second image. For example, the one or more processors may be configured to combine the first and second images at least in part by determining an arithmetic or geometric average of the first image and the second image. Additionally or alternatively, the one or more processors may be configured to combine the first and second images at least in part by determining a weighted average of the first image and the second image. In some variations, such weighted averaging may include determining one or more compounding coefficients for the first and second images, where the first and second images may be combined based on the one or more compounding coefficients.

For example, in some variations, the one or more processors may be configured to determine one or more compounding coefficients at least in part by transforming the first and second images to first and second transform domain images using at least one transformation operator, determining one or more transform domain compounding coefficients for the first and second transform domain images, and inverse transforming the one or more transform domain compounding coefficients to determine the one or more compounding coefficients for the first and second images. The transform domain compounding coefficients may be determined, for example, at least in part by applying one or more coefficient compounding rules (e.g., predetermined, heuristic-based, or learned rules, etc.) to the first and second transform domain images. The transformation operator may include any suitable kind of transformation that supports 1:1 forward and backward transformations (e.g., Fourier Transform, a Discrete Wavelet Transform (DWT), a Discrete Cosine Transform (DCT), or a Wave Atom Transform).

In some variations, the one or more processors may additionally or alternatively be configured to determine one or more compounding coefficients at least in part by determining a first image quality factor map for the first image and a second image quality factor map for the second image, and determining a first compounding coefficient for the first image based on the first image quality factor map, and a second compounding coefficient for the second image based on the second image quality factor map.

Additionally or alternatively, in some variations, the one or more processors may be configured to determine one or more compounding coefficients at least in part by determining a local entropy of each pixel in the first image and a local entropy of each pixel in the second image, and determining one or more compounding coefficients based on the determined local entropies.

Other suitable techniques for determining compounding coefficients include determining one or more compounding coefficients at least in part by applying a linear filter (e.g., Difference of Gaussian filter) to each of the first and second images for estimating and weighting image content, determining one or more compounding coefficients as a function of imaging depth, and/or applying a saturation mask that reduces weight (e.g., compounding coefficient) of at least a portion of the first image and/or second image that has exceeded a predetermined saturation threshold.

In other words, the one or more processors may be configured to combine images from different types of sensors in the mixed transducer array using one or more suitable compounding techniques as described herein, including, for example, one or more of arithmetic averaging, geometric averaging, transform domain compounding, image quality factor-based (IQF) compounding, local entropy weighted compounding, image content weighted compounding, depth dependent weighted compounding, or saturation masking, etc.

DETAILED DESCRIPTION

Figure 1:
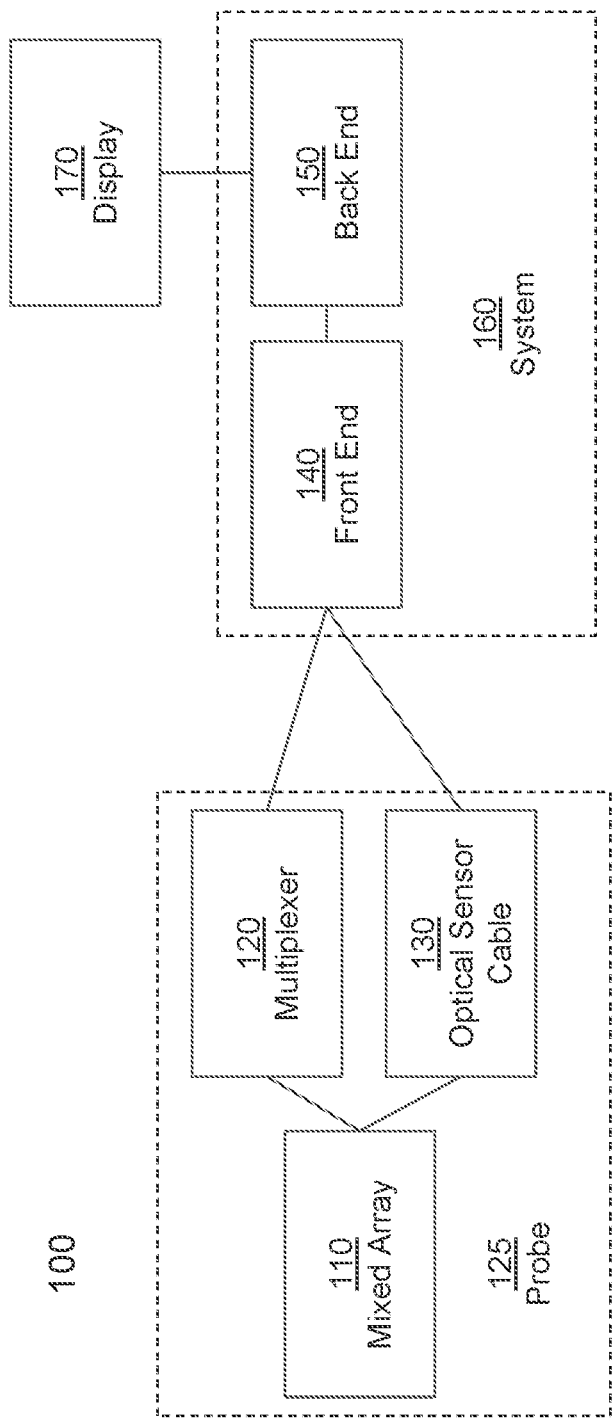
FIG. 1 is a block diagram of an exemplary image compounding system with a mixed array.

Non-limiting examples of various aspects and variations of the invention are described herein and illustrated in the accompanying drawings.

Described herein are methods and devices for compounding (e.g., combining) images acquired using mixed arrays that include multiple types of array elements. Mixed arrays described herein include one or more array elements of a first type and one or more array elements of a second type different from the first type. The one or more array elements of the first type may be used to form a first image, while the one or more array elements of the second type may be used to form a second image. The first type may include non-optical transducer such as a piezoelectric transducer, a single crystal material transducer, a piezoelectric micromachined ultrasound transducer (PMUT), and/or a capacitive micromachined ultrasonic transducer (CMUT), etc. The second type may include an optical sensor, which may be an interference-based optical sensor such as an optical resonator (e.g., a whispering gallery mode (WGM) optical resonator or photonic integrated circuit (PIC) optical resonator) or an optical interferometer. The optical sensor may have any suitable shape. For example, the optical sensor may be a microbubble resonator, a microsphere resonator, a microtoroid resonator, microring resonators, a microbottle resonator, a microcylinder resonator and/or a microdisk optical resonator, etc. The optical sensors have high sensitivity and/or broad bandwidth in reception of ultrasound signals compared to other types of ultrasound sensors.

Various suitable combinations of non-optical transducers and one or more types of optical sensors may be included in the mixed transducer array. For example, in some variations, the array elements of the first type may include a non-optical transducer, and the array elements of the second type may include an optical sensor. The one or more array elements of the first type may include non-optical transducers (non-optical sub-array) for transmitting acoustic signals and/or detecting acoustic echoes to form a first image. The one or more array elements of the second type (e.g., optical sensors in an optical sub-array) may be used to detect acoustic echoes (e.g., full spectrum, baseband, subharmonic, superharmonic, and/or differential harmonic) that can be used to form a second image. The second image that is generated by highly sensitive and/or broad bandwidth optical sensors may be used independently or can be combined with the first image to form an even further improved image. Because of the high sensitivity and broad bandwidth of optical resonators, the image produced by optical sensors may have improved spatial resolution, improved contrast resolution, improved penetration depth, improved signal-to-noise ratio (SNR), improved tissue harmonic imaging, and/or improved Doppler sensitivity. However, because the optical sub-array and the non-optical sub-array intrinsically have different characteristics, compounded images produced by combining images generated using signals produced by different type of sensors may have more features, better image quality and provide a more complete understanding of the underlying imaging target.

Moreover, the optical sensors do not generate ultrasound waves and therefore are used together in mixed arrays with other transducers (e.g., piezoelectric, CMUT, and/or the like) that do generate ultrasound waves. The mixed arrays can be arranged in various configurations and include sensor elements with various noise levels, amplitude responses, phase delays, frequency ranges, and/or the like. Consequently, conventional beamforming methods and devices that are generally used for probes with one type of sensor are not optimal for probes that use mixed arrays of multiple types of sensors. The optical resonators described herein may have ultra-high quality factor ($10^3$, $10^5$, $10^7$, $10^9$ and/or the like) and hence ultra-high sensitivity for ultrasound detection but smaller dynamic range. Such ultra-high quality factor optical resonators may be particularly suitable for ultra-deep imaging but could suffer from undesirable non-linear distortion in near field. On the other hand, the optical resonators can be designed to have a lower quality factor and hence a lower sensitivity compared to the optical resonators with ultra-high quality factor. Such lower quality factor optical resonators may be particularly suitable for imaging in the near field without the undesirable nonlinear distortion. Moreover, the optical resonators may support many different resonant modes. Therefore, an operation mode of the optical resonators can be switched from a first operation mode to a second operation mode, for example, by switching the wavelength of a laser source coupled to the optical resonators. In some variations, an image compounding system may operate the optical resonators in the ultra-high quality factor operation mode at a first time and in the low quality factor operation mode at a second time. In some variations, an image compounding system can operate a first set of the optical resonators in ultra-high quality factor operation mode and a second set of the optical resonators in low quality factor operation mode. In addition, sub-arrays consisting of different types of optical resonators can be deployed in the same image compounding system used to produce different images showing different aspects of the target. Combining images produced by different optical resonators or by operating optical resonators in different operation modes using compounding algorithms such as those described herein can produce or otherwise generate images with a better image quality than images produced or generated by a single type of sensor.

Accordingly, in some variations, the array elements of the second type may include optical resonator sensors with different characteristics (e.g., different design and/or different operating parameters). For example, in some variations, the array elements of the second type may include one or more high quality factor (high Q) optical resonators, and one or more low quality (low Q) optical resonators. Additionally or alternatively, the array elements of the second type may include one or more tunable optical resonators configured to operate as a high Q optical resonator, and one or more tunable optical resonators configured to operate as a low Q optical resonator. For example, such tunable optical resonators may be selectively operable in a high Q or low Q mode, depending on imaging settings, etc. Additionally or alternatively, the array elements of the second type may include one or more optical resonator sensors that are designed for wide bandwidth, and one or more optical resonator sensors that are designed for ultra-high sensitivity.

Furthermore, in some variations, the mixed transducer array may include a combination of one or more non-optical transducers and multiple types of optical sensors. Thus, different kinds of input images (e.g., from non-optical transducers and/or from one or more different kinds of optical sensors) may be combined using image compounding systems and methods such as those described herein, to obtain a compounded image of better quality than any individual input image.

Image Compounding Systems

FIG. 1 is a block diagram of an exemplary image compounding system 100 with a mixed array. The image compounding system 100 includes a probe 125, an imaging system 160, and a display 170. The probe 125 may be operatively coupled to the imaging system 160. The probe 125 may receive and/or transmit a set of signals (e.g., electrical signals, electromagnetic signals, optical signals, etc.) from/to the imaging system 160. The probe 125 includes a mixed array 110 that may receive and/or transmit a set of signals (e.g., acoustic signals, etc.) from/to a medium for use in forming an image. The imaging system 160 may include a front end 140 and a back end 150 that may collectively determine physical parameters (e.g., timing, location, angle, intensity, and/or the like) of signals transmitted to the probe (e.g., via one or more transmit channels), and post-process signals received by the probe 125 (e.g., via one or more receive channels) to form an image. The imaging system 160 may also be coupled to the display 170 to transmit a set of signals (e.g., electrical signals, electromagnetic signals, etc.) to the display 170. For example, in some variations, the display 170 may be configured to display the image produced by the imaging system 160 (e.g., in a graphical user interface (GUI)). Additionally or alternatively, the imaging system 160 may receive signals from the display 170. For example, the display 170 may further include an interactive interface (e.g., touch screen, keyboard, motion sensor, and/or the like) to receive commands from a user of the image compounding system 100, such as to control operation of the image compounding system 100.

As shown in FIG. 1, the probe 125 may include a mixed array 110, a multiplexer 120, and an optical sensor cable 130. The mixed array 110 may include one or more non-optical array elements (e.g., PZT transducers, CMUT transducers, etc.) and one or more optical array elements (e.g., optical sensors such as WGM resonators). The non-optical transducers may be configured to transmit acoustic waves, and in some variations may be configured to additionally receive and detect acoustic echoes in response to transmitted acoustic waves. The optical sensors may be configured to receive and detect echo signals with high sensitivity and/or broad bandwidth response. In some variations the mixed array may be similar to any of the mixed arrays described in International Patent App. No. PCT/US2021/033715, which is incorporated herein in its entirety by this reference. In some variations, the mixed array may be configured to perform harmonic imaging as described in International Patent App. No. PCT/US2021/039551, which is incorporated herein in its entirety by this reference. In some variations, the probe 125 may be configured to iteratively scan across a field of view by using the mixed array 110. In some variations, signals from the mixed arrays may be combined through a synthetic aperture technique, such as techniques described in International Patent App. No. PCT/US2021/049226, which is incorporated herein in its entirety by this reference. Such signals may be used to generate images using the optical sensors and/or the non-optical transducers, as described in further detail below.

The mixed array 110 may include an array of transducer elements and may be configured for operation in a 1 dimensional (1D) configuration, a 1.25 dimensional (1.25D) array configuration, a 1.5 dimensional (1.5D) array configuration, a 1.75 dimensional (1.75D) array configuration, or a 2 dimensional (2D) array configuration. Generally, dimensionality of the ultrasound sensor array relates to the range of elevation beam width (or elevation beam slice thickness) that is achievable when imaging with the ultrasound sensor array, and how much control the system over the sensor array's elevation beam size, foci, and/or steering throughout an imaging field (e.g., throughout imaging depth). A 1D array has only one row of elements in elevation dimension and a fixed elevation aperture size. A 1.25D array has multiple rows of elements in elevation dimension and a variable elevation aperture size, but a fixed elevation focal point via an acoustic lens. A 1.5D array has multiple rows of elements in elevation dimension, a variable elevation aperture size, and a variable elevation focus via electronic delay control. A 1.75D array is a 1.5D array with additional elevation beam steering capability. A 2D array has large numbers of elements in both lateral and elevation dimensions to satisfy the minimum pitch requirement for large beam steering angles in both the lateral and elevation directions.

In some variations, the image compounding system may be configured to turn a 1.5D array configuration or a 2D array configuration into a 1D array configuration. The mixed array 110 may include a large number (e.g., 16, 32, 64, 128, 256, 1024, 4096, 8192, 16384, and/or the like) of elements. In some variations, the mixed array 110 may be arranged in a rectangular configuration and may include N×M elements, where N is the number of rows and M is the number of columns. In some variations, for example, the mixed array 110 includes one or more array elements of a first type and one or more array elements of a second type, where the first type may be a piezoelectric transducer or other non-optical transducer configured to transmit ultrasound waves and the second type may be an optical sensor such as an optical resonator. Non-optical transducers and optical sensors may be collectively positioned in a rectangular arrangement, a curved arrangement, a circular arrangement, or a sparse array arrangement.

The non-optical transducer(s) in the mixed array 110 may include, for example, a lead zirconate titanate (PZT) transducer(s), a polymer thick film (PTF) sensor(s), a polyvinylidene fluoride (PVDF) sensor(s), a capacitive micromachined ultrasound transducer (CMUT)(s), a piezoelectric micromachined ultrasound transducer (PMUT) (s), a transducer(s) based on single crystal materials (e.g., $LiNbO_3$ (LN), $Pb(Mg_{1/3}Nb_{2/3})$—$PbTiO_3$ (PMN—PT), and $Pb(In_{1/2}Nb_{1/2})$—$Pb(Mg_{13}Nb_{2/3})$—$PbTiO_3$ (PIN—PMN—PT)), and/or any transducer suitable for acoustic sensing.

The optical sensor may be or include, for example, an interference-based optical sensor such as an optical interferometer or optical resonator (e.g., whispering gallery mode (WGM) optical resonator). In variations in which the optical sensor is an optical resonator, the optical sensor may have any suitable shape or form (e.g., a microring resonator, a microsphere resonator, a microtoroid resonator, a microbubble resonator, a fiber-based resonator, an integrated photonic resonator, a micro-disk resonator, and/or the like). In some variations, the optical sensors may be/include, for example, Fabry-Perot (FP) resonators, fiber-based resonators (e.g., fiber ring resonators), photonics crystal resonators, waveguide resonators, or any other suitable optical resonator that may localize optical energy in space and time. For example, in some variations an optical resonator may be similar to any of the optical resonators described in International Patent App. Nos. PCT/US2020/064094 and PCT/US2021/022412, each of which is incorporated herein in its entirety by this reference.

The optical resonators may include a closed loop of a transparent medium (e.g., glass, transparent polymer, silicon nitride, titanium dioxide, or any other material that is suitably optically transparent at an operation wavelength of the optical resonator) that allows some permitted frequencies of light to continuously propagate inside the closed loop, and to store optical energy of the permitted frequencies of light in the closed loop. The aforementioned is equivalent to say that the optical resonators may permit a propagation of modes (e.g., whispering gallery modes (WGMs)) traveling the surface of the optical resonators and corresponding to the permitted frequencies to circulate the circumference of the resonator. Each mode corresponds to propagation of at least one frequency of light from the permitted frequencies of light. The permitted frequencies of light and the quality factor of the optical resonators described herein may be based at least in part on geometrical parameters of the optical resonator, refractive index of the transparent medium, and refractive indices of an environment surrounding the optical resonator.

An optical resonator as described herein may have a set of resonant frequencies including a first subset of resonator frequencies and a second subset of resonant frequencies. In some variation, the optical resonator may be operated at the first subset of resonant frequencies with high quality factors. Alternatively or in addition, in some variations, the optical resonator may be operated at the second subset of resonant frequencies with low quality factors. The high quality factor subset of resonant frequencies may be suitable for operating at highly sensitive sensing probes (or sub-arrays) while the low quality factor subset of resonant frequencies may be suitable for high dynamic range applications.

In some variations, the sensitivity of the optical resonator may be controlled by tuning geometrical and/or characteristic material parameters of the optical resonator for tunability of the quality factor of the optical resonator. In some variations, the space inside and/or around the optical resonators may be filled with an ultrasonic enhancement material, such as for example, polyvinylidene fluoride, parylene, polystyrene, and/or the like. The ultrasonic enhancement material may increase sensitivity of the optical resonators.

The optical resonators may be coupled to other components to receive/transmit light. In some implementations, the optical resonator(s) may be operatively coupled, via an optical medium (e.g., optical fiber, a tapered optical fiber, free space medium, and/or the like), to a light source (e.g., a laser, a tunable laser, an erbium doped fiber amplifier, and/or the like) and/or a photodetector (e.g., a p-doped/intrinsic/n-doped (PIN) diode). Acousto-optic systems based on optical resonators may directly measure ultrasonic waves through the photo-elastic effect and/or physical deformation of the resonator(s) in response to the ultrasonic waves (e.g., ultrasonic echoes). Therefore, the optical resonators may be considered as optoacoustic transducers that may convert mechanical energy (e.g., acoustic energy) to optical energy. For example, in the presence of ultrasonic (or any pressure) waves, the modes traveling in a resonator may undergo a spectral shift or amplitude change caused by changes in the refractive index and/or shape of the resonator. The spectral change may be easily monitored and analyzed in the spectral domain using the photodetector. The amplitude change may also be detected by the photodetector. The photodetector eventually converts the optical energy (i.e., optical signal) propagating in the optical resonators and the optical fiber into electrical energy (i.e. electrical signal) suitable for processing with electronic circuitry. Additional spatial and other information may furthermore be derived by monitoring and analyzing optical response of optical resonators among mixed arrays. Exemplary mixed transducer arrays are described herein. Additionally or alternatively, signals from the optical resonator(s) can be processed by optical circuitry before being converted to electrical energy by photodetector(s).

The mixed array 110 may have the one or more non-optical array elements (e.g., ultrasound transducer or other non-optical transducer) and the one or more optical array elements (e.g., optical sensor such as a WGM optical resonator) arranged in various configurations (similar to any of the mixed arrays described in International Patent App. No. PCT/US2021/033715, which was incorporated above). For example, in some configurations, the non-optical and optical array elements may be collectively positioned in a rectangular array including a number of rows and a number of columns. The rectangular array may include N×M sensor elements, where N is the number of rows and M is the number of columns and are both integers. In some implementations such as for a 2D array, the number of rows and/or the number of columns may be greater than 31 rows and/or 31 columns. For example, a 2D mixed array may include 64×96=6,144 sensor elements.

In some variations, mixed array 110 may include optical sensors of multiple different types. For example, as further described below, different types of optical sensors may include a broad bandwidth optical resonator and an ultra-sensitive optical resonator. As another example, the mixed array 110 may include one or more high quality factor (high Q) optical resonators, and one or more low quality (low Q) optical resonators. Additionally or alternatively, mixed array 110 may include one or more tunable optical resonators configured to operate in different quality factor modes. For example, the tunable optical resonators can be operated at a low quality factor (low Q) operation mode for a high dynamic response or a high quality factor (high Q) operation mode for a sensitive response. In some implementations, the tunable optical resonators may be or include a first set of tunable optical resonators and a second set of tunable optical resonators that may be operated at different operation modes. In some implementations, the tunable optical resonators may be operated at the high Q operation mode at a first time interval and operated at the low Q operation mode at a second time interval. In other words, in some variations the mixed array 110 may include one or more tunable optical resonators configured to operate as a high Q optical resonator, and/or one or more tunable optical resonators configured to operate as a low Q optical resonator. For example, such tunable optical resonators may be selectively operable in a high Q or low Q mode, depending on imaging settings, etc.

In some configurations, a spatial distribution of positions of multiple array element types may be random. By using the sparse spatial distribution of array elements, generation of grating lobes in an image produced by the mixed array may be reduced and/or prevented. A spatial distribution of the array elements of a first type may be the same, similar to, or different from, a spatial distribution of the array elements of a second type. In some configurations, a spatial distribution of positions of the array elements of a first type and a second type may follow a dispositioning pattern (e.g., be the same, shift to the right by one cell among sensor elements, shift to down by two cells among sensor elements). In some instances, the one or more array elements of a second type may be smaller than or the same as the one or more array elements of a first type.

The non-optical transducers in the mixed array 110 may be operatively coupled to the multiplexer 120 that handles transmitted and/or received electrical signals between the imaging system 160 and the non-optical transducers. The optical sensors in the mixed array 110 may be operatively coupled to the optical sensor cable 130 that handles transmitted and/or received optical signals between the imaging system 160 and the optical sensors.

The multiplexer 120 functions to selectively connect individual system channels to desired array elements. The multiplexer 120 may include analog switches. The analog switches may include a large number of high voltage analog switches. Each analog switch may be connected to an individual system channel. As a result, the multiplexer 120 may selectively connect an individual system channel from a set of system channels of the imaging system 160 to a desired transducer element of the mixed array 110.

The optical sensor cable 130 may include a dedicated optical path for transmitting and/or receiving optical signals to and/or from the optical sensors. The optical sensor cable 130 may include one or more optical waveguides such as, for example, fiber optical cable(s). Characteristics of the optical sensor cable 130 may depend upon type of the optical signals, type of optical sensors, and/or an arrangement of optical sensors. In some configurations, multiple optical sensors (e.g., the entire sub-array of the optical sensors, or any two or more optical sensors forming a portion thereof)

may be optically coupled to a single optical waveguide. Accordingly, signals from multiple optical sensors may be coupled into and communicated by a single optical waveguide. In some configurations, the sub-array of the optical sensors may be optically coupled to an array of optical waveguides in a 1:1 ratio (e.g., each optical sensor may be coupled to a respective optical waveguide). Accordingly, optical signals from the sub-array of the optical sensors may be coupled to and communicated by one or more optical waveguides in the optical sensor cable 130 to the imaging system 160.

The imaging system 160 may include a front end 140 and a back end 150. Generally, the front end 140 interfaces with the probe 125 to generate acoustic beams and receive electrical and/or optical signals. For example, the front end 140 may drive non-optical transducers (e.g., transducers) in the probe to transmit ultrasound signals in predefined beam patterns, and may receive the reflected ultrasound signals from the non-optical transducers and optical sensors in the mixed array in the probe. The front end may also be tasked to perform both transmit and receive beamforming. The back end 150 may include one or more processors to process signals received from the mixed array 110 via the front end to generate images, a memory operatively coupled to the processor to store the images, and/or a communication interface to present the images to a user (e.g., via graphical user interface). For example, the back end 150 may receive separately reconstructed images from the receive beamformer in the front end, perform additional back end processes, and conduct image compounding operations. Various back end processes may be involved in the image formation, including digital signal processing (DSP), digital scan conversion (DSC), envelope detection, and/or the like. To implement image compounding using optical sensors, the image compounding system may include specific implementations of a back end process for storing, analyzing, combining, and transmitting data, signals, and/or images. Such specific implementations are shown and described below with respect to FIGS. 2-5.

The display 170 may display a set of images generated by the imaging system 160. In some variations, the display 170 may additionally or alternatively include an interactive user interface (e.g., a touch screen) and be configured to transmit a set of commands (e.g., pause, resume, and/or the like) to the imaging system 160. In some variations, the image compounding system 100 may further include a set of one or more ancillary devices (not shown) used to input information to the image compounding system 100 or output information from the image compounding system 100. The set of ancillary devices may include, for example, a keyboard(s), a mouse(s), a monitor(s), a webcam(s), a microphone(s), a touch screen(s), a printer(s), a scanner(s), a virtual reality (VR) head-mounted display(s), a joystick(s), a biometric reader(s), and/or the like (not shown).

Figure 2:
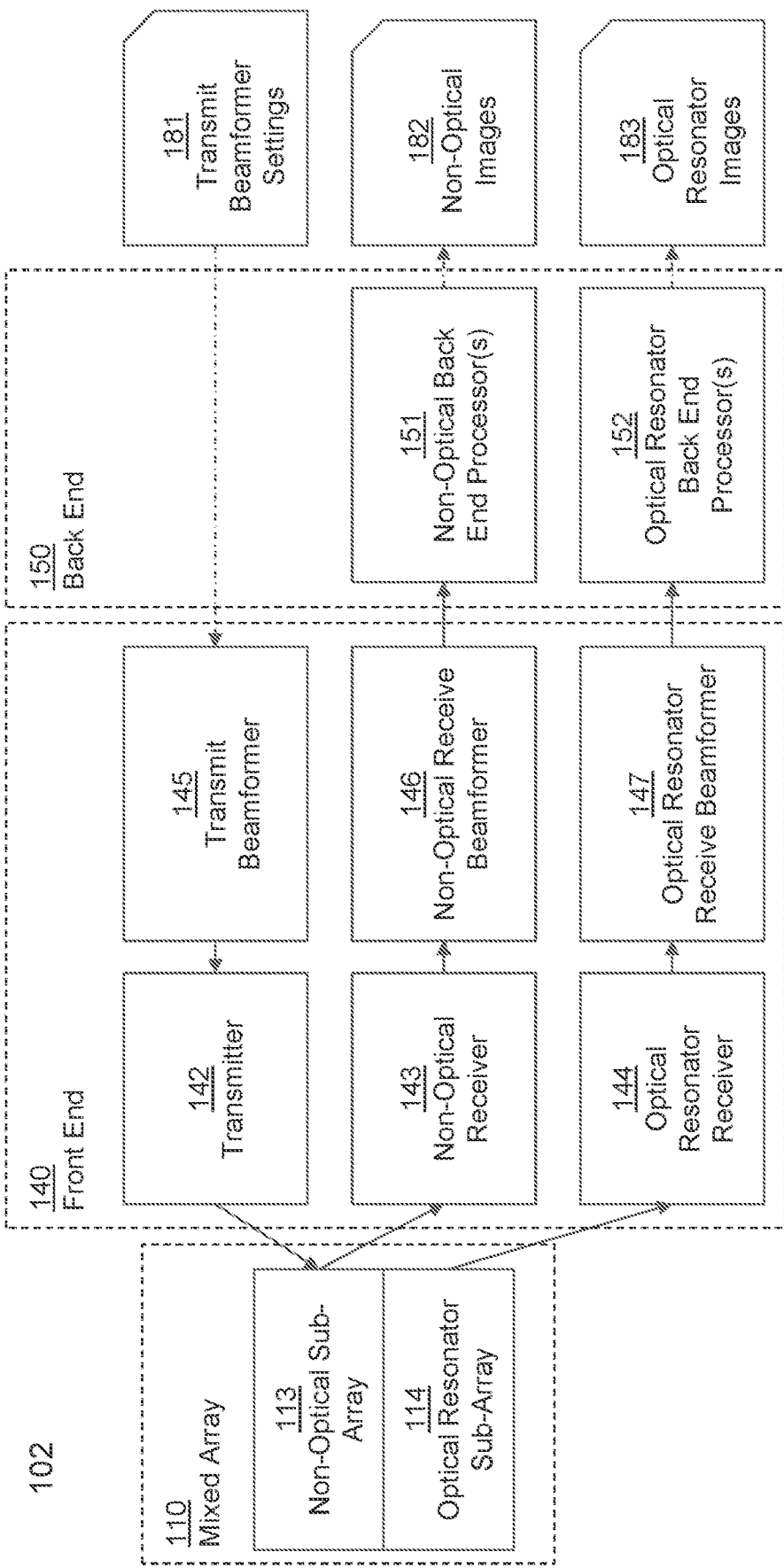
FIG. 2 is a block diagram of an exemplary image compounding system with a mixed array.

FIG. 2 shows a block diagram of an exemplary image compounding system 102 with a mixed array 110. As shown, the mixed array 110 may include a non-optical sub-array 113 and an optical resonator sub-array 114. The front end 140 may include a transmitter 142, a non-optical receiver 143, an optical resonator receiver 144, a transmit beamformer 145, a non-optical receive beamformer 146, and an optical resonator receive beamformer 147. The back end 150 may include non-optical back end processor(s) 151 and optical resonator back end processor(s) 152. The non-optical back end processor(s) 151 and optical resonator back end processor(s) 152 may involve performing including digital signal processing (DSP), digital scan conversion (DSC), envelope detection, and/or the like.

The transmit beamformer 145 generates various transmit waveforms based on transmit beamformer settings 181. The waveforms may be amplified by the transmitter 142 that may include analog circuitry, digital circuitry, and/or computer systems, before being applied to the non-optical sub-array 113. After receiving the waveforms and/or amplified waveforms by the transmitter 142 the non-optical sub-array 113 may generate a set of acoustic waves (e.g., ultrasound signals) toward a target. The acoustic waves insonify the target, which in turn reflects part of the acoustic waves (i.e., echo signals) back to the mixed array probe. The non-optical receiver 143 receives the echo signals detected by the non-optical transducers and processes them to produce digitized signals as the output. The signals detected by the optical resonator sub-array 114 may be processed and digitized by the optical resonator receiver 144. The non-optical resonator receive beamformer 146, the optical receive beamformer 147, the non-optical back end processors 151, and the optical back end processors 152, use the signals processed by the two receivers to form non-optical images 182 and optical resonator images 183. The non-optical images 182 and optical resonator images 183 often have different characteristics. The different characteristics of non-optical images 182 and optical resonator images 183 may depend on factors including an arrangement of sensing elements (non-optical transducer or optical resonator) in the mixed array, physical parameters of the sensing elements, and/or the like.

Figure 3:
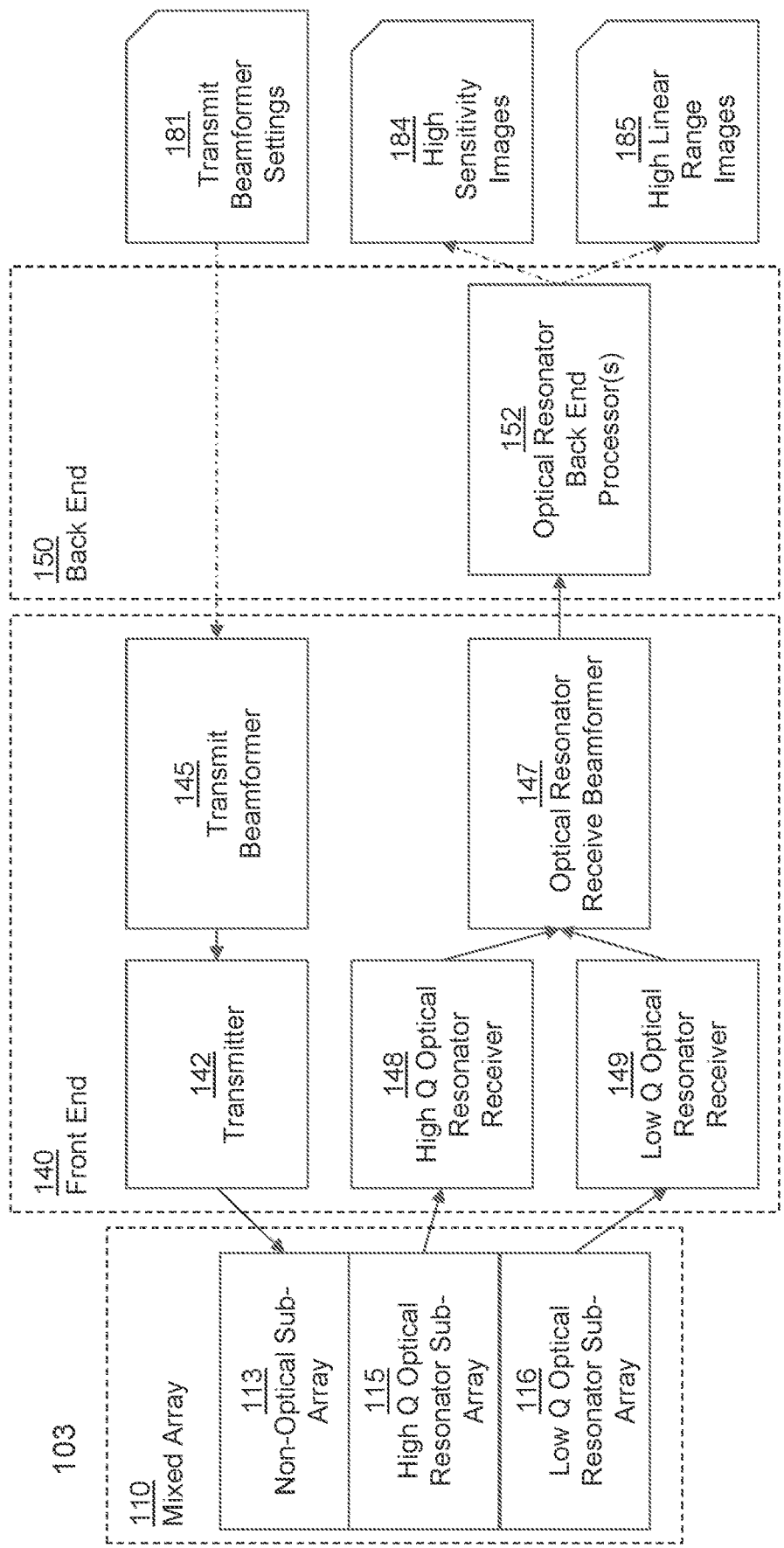
FIG. 3 is a block diagram of an exemplary image compounding system with a mixed array.

FIG. 3 shows a block diagram of an exemplary image compounding system 103 with a mixed array 110 that includes optical resonator sensors including sub-arrays with different quality factors (Q factors). As shown, the mixed array 110 may include a non-optical sub-array 113, a high quality factor (high Q) optical resonator sub-array 115, and a low quality factor (low Q) optical resonator sub-array 116. The front end 140 may include a transmit beamformer 145, a transmitter 142, a high Q optical resonator receiver 148 that receives signals from the high Q optical resonator sub-array, a low Q optical resonator receiver 149 that receives signals from the low Q optical resonator sub-array, and an optical resonator receive beamformer 147. Although separate optical resonator receivers (high Q optical resonator receiver 148 and low Q optical resonator receiver 149) are shown in FIG. 3 as receiving signals from high Q optical resonators and low Q optical resonators, respectively, it should be understood that in some variations, the receivers 148 and 149 may be replaced by one or more receivers that may receive a wide range of Q factor signals. For example, a single receiver may dynamically be tuned or otherwise configured to receive low Q signals (e.g., in one or more "low Q" modes) and tuned or otherwise configured to receive high Q signals (e.g., in one or more "high Q" modes). The single receiver may be dynamically configured across a spectrum of Q factors, or may be operable among different discrete modes corresponding to respective ranges of Q factors. The back end 150 may include one or more optical resonator back end processors 152. The optical resonator back end processors 152 may involve performing one or more techniques including digital signal processing (DSP), digital scan conversion (DSC), envelope detection, and/or the like.

Signals acquired by the high Q optical resonator sub-array 115 may generate one or more high sensitivity images 184, where features with lower reflectivity or weaker signals from deep depth may be better visualized and features with high reflectivity or strong signals from shallow depth may be saturated. On the other hand, the low Q optical resonator sub-array generates one or more high dynamic range images 185 that may miss smaller and lower reflective features or weaker signals from deep depth. The one or more high sensitivity images 184 and the one or more high dynamic range images 185 may be used in the optical resonator back end processor(s) 152 to generate a compound image that includes the advantages of signals of each of the high Q and low Q optical resonator sub-arrays.

As shown in FIG. 3, in some variations, the high Q optical resonator sub-array 115 and the low Q optical resonator sub-array 116 may share the optical resonator receive beamformer 147 and the optical resonator back end processor(s) 152. Alternatively, in some variations, the high Q optical resonator sub-array 115 and the low Q optical resonator sub-array 116 may have different respective receive beamformers and/or different respective back end processor(s). For example, the high Q optical resonator sub-array 115 may be operatively coupled to a high Q optical resonator receive beamformer (not shown) and a high Q optical resonator back end process (not shown), and the low Q optical resonator sub-array 116 may be operatively coupled to a low Q optical resonator receive beamformer (not shown) and a low Q optical resonator back end process (not shown).

In some variations, the front end 140 may further include a non-optical receiver and a non-optical receive beamformer (e.g., non-optical receiver 143 and non-optical receive beamformer 146 as shown and described with respect to FIG. 2). Consequently, the back end 150 may also include non-optical back end processor(s) such as non-optical back end processor(s) 151 that produce non-optical images 182 as shown and described with respect FIG. 2. Therefore, the image compounding system 103 may be configured to form a compound image based on high sensitivity images 184 and high dynamic range images 185, and optionally additionally based on non-optical images 182.

Figure 4:
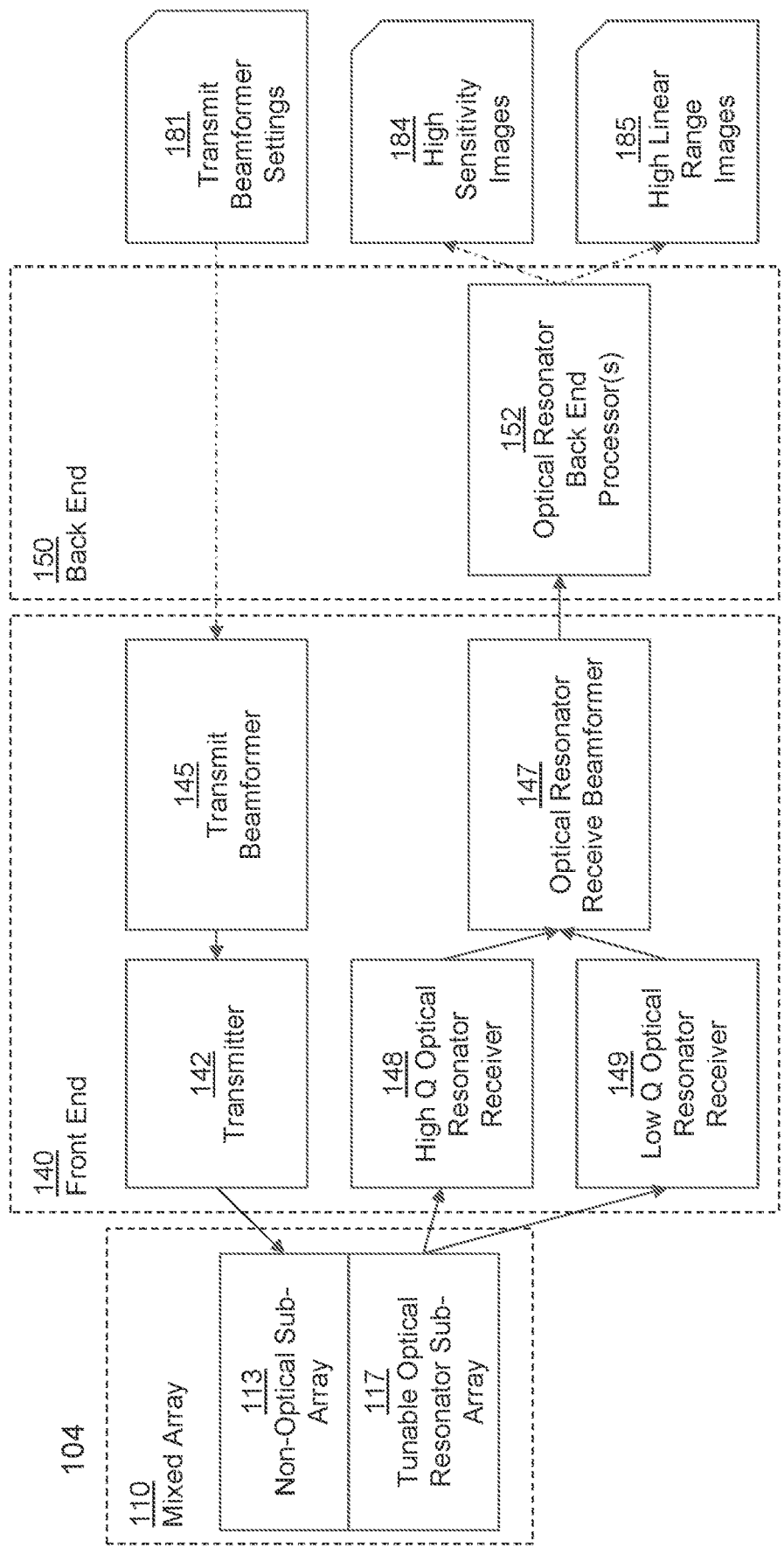
FIG. 4 is a block diagram of an exemplary image compounding system with a mixed array.

FIG. 4 shows a block diagram of an exemplary image compounding system 104 with a mixed array 110 that is similar to the image compounding system 103 shown and described above with respect to FIG. 3, except that the mixed array 110 includes a tunable optical resonator sub-array 117 that is operable in two or more modes with different Q factor values. Tuning for different modes may be accomplished by, for example, selectively modifying ambient temperature around the mixed array 110, and/or changing the optical wavelength. Such a tunable optical resonator sub-array 117 may be used to acquire both high sensitivity images and high dynamic range images. For example, in some variations, at least one optical resonator in the tunable optical resonator sub-array 117 may receive signals at multiple times in response to different sets of transmission sequences, where the at least one optical resonator operates in a high Q mode at one time, and in a low Q mode at a different time. In other words, in some variations, at least a portion of the tunable optical resonator sub-array 117 may be operated at a first time interval and a second time interval not overlapping the first time interval, where at least a portion of the tunable optical resonator sub-array 117 may be operated as a high Q optical resonator at the first time interval to generate the high sensitivity images 184, and as a low Q optical resonator at the second time interval to generate the high dynamic range images 185. In some variations, at least one tunable optical resonator may operate in a high Q mode before operating in a low Q mode. Additionally or alternatively, at least one tunable optical resonator may operate in a low Q mode before operating in a high Q mode. At least two sets of transmission sequences may be performed to insonify the target multiple times to acquire signals from both the high Q optical resonator receiver 148 and the low Q optical resonator receiver.

Additionally or alternatively, in some variations, at least a first portion (e.g., a first set) of the tunable optical resonator sub-array 117 may be consistently designated to operate in a high Q mode, and at least a second portion (e.g., a second set) of the tunable optical resonator sub-array 117 may be consistently designated to operate in a low Q mode. Signals from the first portion of the tunable optical resonators may be received by the high Q optical resonator receiver 148, and signals from the second portion of the tunable optical resonators may be received by the low Q optical resonator receiver 149. In some variations in which the tunable optical resonator sub-array simultaneously includes some optical resonators tuned to operate in a high Q mode and some optical resonators tuned to operate in a low Q mode, the mixed array 104 may be functionally similar to the mixed array 103 shown and described above with respect to FIG. 3. Similar to that described above with respect to FIG. 3, although separate optical resonator receivers (high Q optical resonator receiver 148 and low Q optical resonator receiver 149) are shown in FIG. 4 as receiving high Q signals and low Q signals, respectively, it should be understood that in some variations, the receivers 148 and 149 may be replaced by one or more receivers that may receive a wide range of Q factor signals. For example, a single receiver may dynamically be tuned or otherwise configured to receive low Q signals (e.g., in one or more "low Q" modes) and tuned or otherwise configured to receive high Q signals (e.g., in one or more "high Q" modes). The single receiver may be dynamically configured across a spectrum of Q factors, or may be operable among different discrete modes corresponding to respective ranges of Q factors.

As shown in FIG. 4, the mixed array 110 may include a non-optical sub-array 113 and a tunable optical resonator sub-array. The front end 140 may include a transmit beamformer 145, a transmitter 142, a high Q optical resonator receiver 148, a low Q optical resonator receiver 149, and an optical resonator receive beamformer 147. The non-optical sub-array 113 in the mixed array 110 may transmit a set of acoustic signals, and the tunable optical resonators sub-array may receive a set of acoustic echoes in response to the acoustic signals. The tunable optical resonator sub-array 117 may be operatively coupled to a photodetector configured to generate a first signal and a second signal, where the first signal includes a readout from at least a portion of the tunable optical resonator sub-array 117 operating in a high Q mode, and the second signal includes a readout from at least a portion of the tunable optical resonator sub-array 117 operating in a low Q mode. The high Q optical resonator receiver 148 and the low Q optical resonator receiver 149 may receive the first signal and the second signal, respectively. The back end 150 may include an optical resonator back end processor(s) 152. The optical resonator back end processor(s) 152 may perform operations including digital signal processing (DSP), digital scan conversion (DSC), envelope detection, and/or the like on the first signal and the second signal to generate high sensitivity images 184 and high dynamic range images 185. The back end 150 may be further configured to combine the high sensitivity images 184 and the high dynamic range images 185 to generate a compound image that includes the advantages of signals of each of the high Q and low Q modes of the tunable optical resonator sub-array 117

In some variations, multiple transmission sequences are transmitted using the transmit beamformer settings 181, the transmit beamformer 145, the transmitter 142, and the non-optical sub-array 113 to insonify a target multiple times. For example, the non-optical sub-array 113 may transmit a first transmission sequence and a second transmission sequence. In response, the tunable optical resonator sub-array 117 may acquire the first signal in response to the first transmission sequence and the second signal in response to the second transmission sequence. The back end may then produce the first image from the first signal and produce the second image from the second signal.

Figure 5:
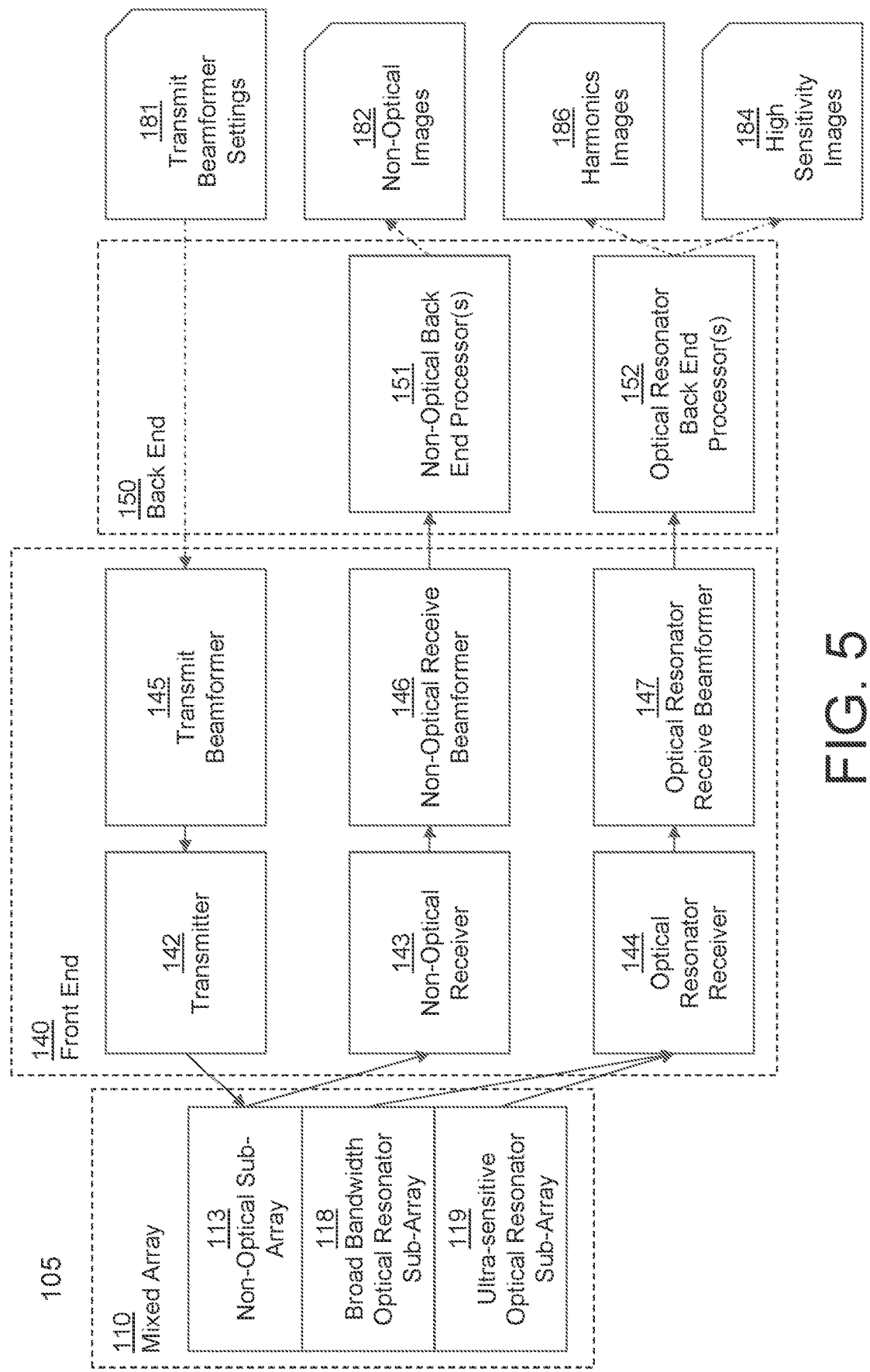
FIG. 5 is a block diagram of an exemplary image compounding system with a mixed array.

FIG. 5 shows a block diagram of an exemplary image compounding system 105 with a mixed array 110 that includes optical resonators in both a sub-array with broad bandwidth and a sub-array with high sensitivity. For example, the mixed array may include a non-optical sub-array 113, a broad bandwidth optical resonator sub-array 118 and an ultra-sensitive optical resonator sub-array 119. The broad bandwidth optical resonator sub-array 118 may capture signal outside of the baseband of the transmitted acoustic waves, such as super-harmonics and subharmonics from tissue and/or contrast agents (e.g., as described in International Patent App. No. PCT/US2021/039551, which was incorporated above by reference). The ultra-sensitive optical resonator sub-array 119 may capture signals from deeper regions in and out of the baseband.

The non-optical sub-array 113 may be operatively coupled to the transmitter 142, which is operatively coupled to the transmit beamformer 145 receiving transmit beamformer settings 181. The non-optical sub-array 113 transmits acoustic signals towards a target and receives acoustic echoes in response to the acoustic signals. The non-optical sub-array 113 may be additionally operatively coupled to the non-optical receiver 143 and the non-optical receive beamformer 146 in the front end 140 to generate a first signal in response to the acoustic echoes received at the non-optical sub-array 113. The non-optical back end processor(s) 151 may analyze the first signal to generate a first image (non-optical image(s) 182) that visualizes the target with conventional spatial resolution and imaging depth. The broad bandwidth optical resonator sub-array 118 and the ultra-sensitive optical resonator sub-array 119 may be operatively coupled to the optical resonator receiver 144 and optical resonator receive beamformer 147. The optical resonator back end processor(s) 152 may be used to process signals from the two optical resonator sub-arrays 118 and 119 to produce one or more images (e.g., fundamental frequency images, super-harmonic images, sub-harmonic images, etc.) and one or more high sensitivity images. For example, a second signal originating from the broad bandwidth optical resonator sub-array 118 may be used to generate a second image (harmonic image(s) 186), and/or a third signal originating from the ultra-sensitive optical resonator sub-array 119 may be used to generate a third image (high sensitivity image(s) 184). Therefore, the image compounding system 105 may achieve enhanced spatial resolution and imaging depth at the same time.

After the first image(s), the second image(s), and/or the third image(s) are separately generated using the first signal, the second signal, and/or the third signal from the non-optical sub-array 113, the broad bandwidth optical resonator sub-array 118, and the ultra-sensitive optical resonator sub-array 119, respectively, an image compounding algorithm may be used to combine the first image, the second image, and/or the third image and produce a compound image as further described below.

Methods of Performing Image Compounding

FIGS. 6-10 described below illustrate aspects of exemplary methods of performing image compounding based on images received from a mixed array described above. Although the methods are primarily described with reference to optical resonator sensors, it should be understood that they may similarly be performed using signals from optical sensors of other kinds (e.g., optical interferometer). The methods of performing image compounding may be executed by an image compounding computing device that is part of (e.g., back end 150 as shown and described with respect to FIGS. 1-5) and/or is operatively coupled to an image compounding system (such as the image compounding system 100 shown and described with respect to FIG. 1). The image compounding computing device may include a set of electronic circuitries such as a processor, a memory, and a communication interface. The processor may include, for example, a hardware based integrated circuit (IC) or any other suitable device to run or execute a set of instructions/codes. For example, the processor may include a general purpose processor, a central processing unit (CPU), an accelerated processing unit (APU), an application specific integrated circuit (ASIC), a microprocessor, a field programmable gate array (FPGA) chip, a graphics processing unit (GPU), a digital signal processing (DSP) chip, and/or the like. The memory may store, for example, code that includes instructions to cause the processor to perform one or more processes or functions (e.g., filtering signals, amplifying signals, phase matching, noise reduction, selecting apertures, and/or the like). The memory may be/include, for example, a memory buffer, a random access memory (RAM), a read-only memory (ROM), a flash drive, a secure digital (SD) memory card, and/or the like. The communication interface may be/include a universal serial bus (USB) interface, a peripheral component interconnect express (PCIe) interface, or a hardware component that is operatively coupled to the processor and/or the memory and may enable communication of the image compounding computing device with components of the image compounding system and/or in some variation, external device and/or network of devices (e.g., the Internet).

The image compounding computing device may include an application as a software stored in the memory and executed by the processor. For example, the application may include code to cause the processor to select aperture, analyze signals, generate an image, and/or the like. Alternatively, the application may be implemented on a hardware-based device. For example, the application may include a digital circuit(s) or an analog circuit(s) that may cause the image compounding computing device to filter signals, amplify signals, and/or delay signals.

Figure 6:
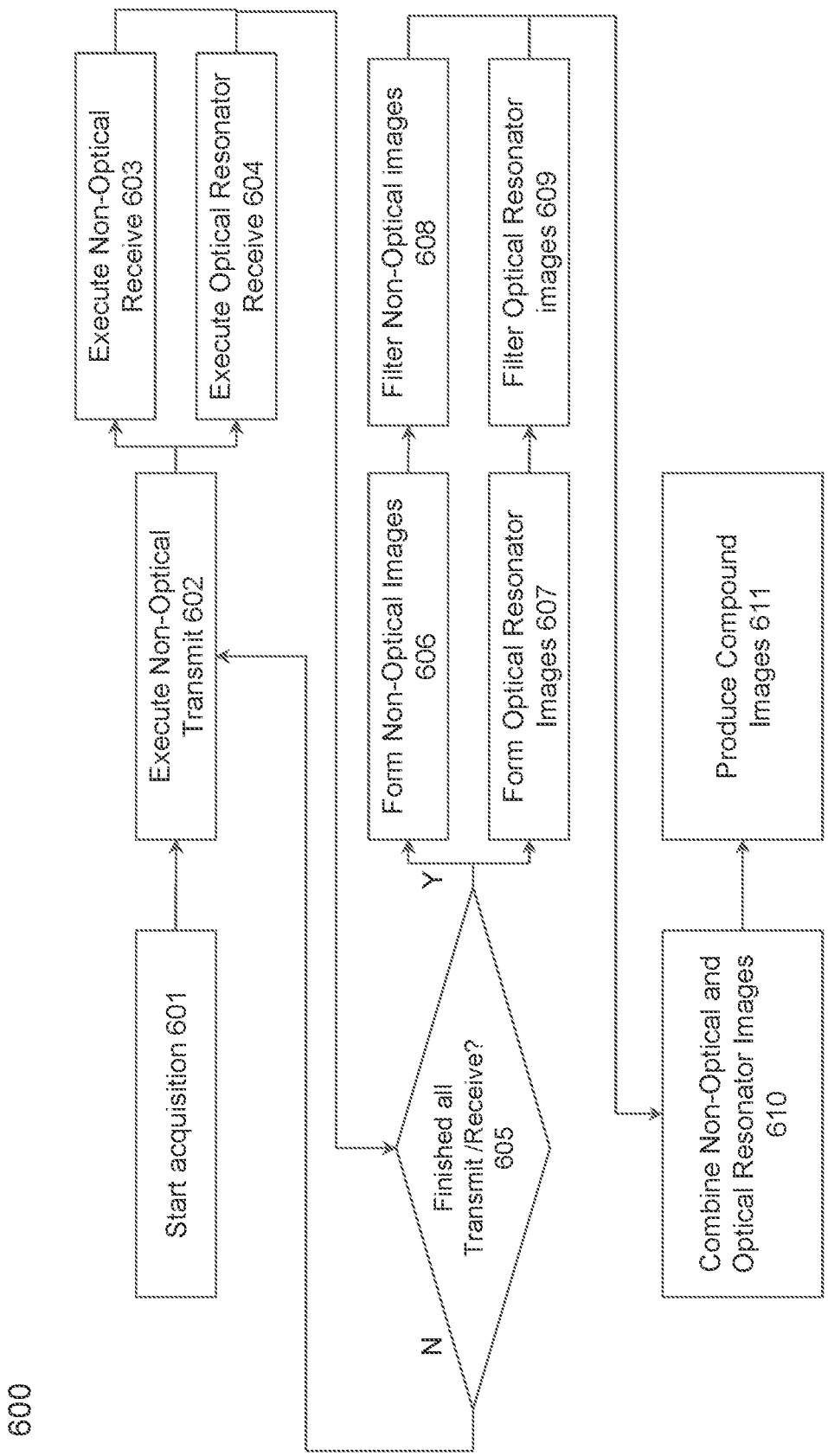
FIG. 6 is a flowchart of an exemplary method of performing image compounding on images acquired by a mixed array.

FIG. 6 is a flowchart of an exemplary method 600 of performing image compounding on images acquired by a mixed array. In some implementations, the method may be performed with the compound imaging system 102 (e.g., back end 150) as shown and described with respect to FIG. 2. The method 600 may include initiating image acquisition (601) (e.g., upon receipt of an indication to begin acquisition). The method 600 may further include transmitting a non-optical signal (602) followed by receiving a non-optical signal (603) and receiving an optical resonator signal (604) (or other optical sensor signal). The method may iterate 602, 603, and/or 604 until all transmit steps desired to transmit acoustic signals from all non-optical array elements and all receive steps to receive acoustic echoes from all non-optical array elements and optical array elements of the mixed array 110 are executed. Once all desired transmission and receiving have been performed for at least one desired compound image (605), the method 600 may further include generating or forming non-optical images (606) and generating or forming optical resonator images (607) using the front end 140 and back end 150 of the compound imaging system 102. The back end 150 may then apply image domain filters to the non-optical images and optical resonator images (608, 609). The image domain filters may be specifically designed according to the image characteristics of each type of images. The method 600 may include combining (e.g., using a compounding algorithm such as those described below) the non-optical images and optical resonator images (610) and producing the compound images (611). Generally, in some variations, the compound images may, for example, be formed utilizing dynamically-determined weight masks with compounding coefficients that indicate which features of the non-optical images and which features of the optical resonator images may be included in each compound image.

Figure 7:
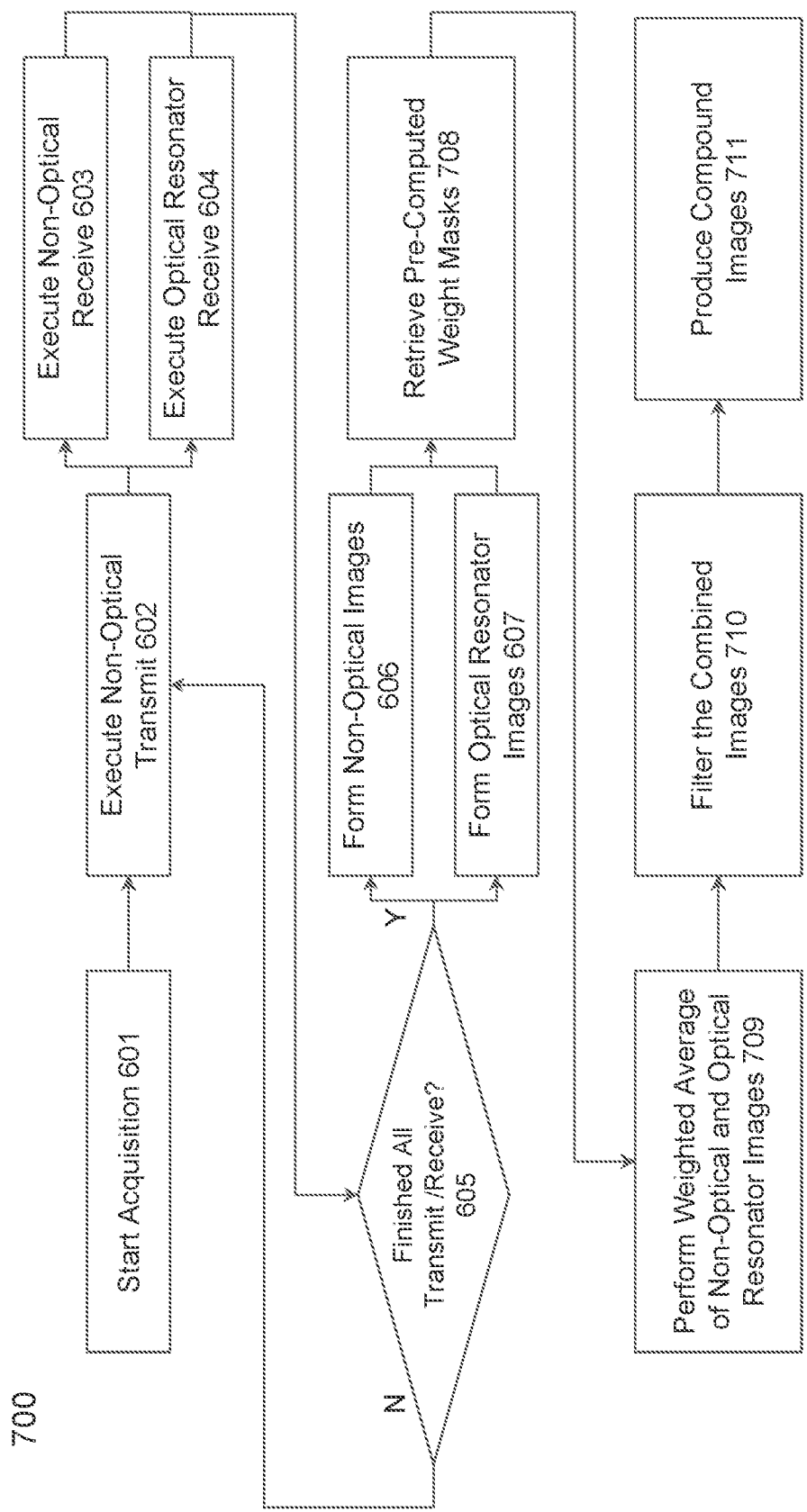
FIG. 7 is a flowchart of an exemplary method of performing image compounding on images acquired by a mixed array.

Additionally or alternatively, in some variations, compound images may be formed utilizing static weight masks that may be pre-determined and stored for use during later image compounding processes. For example, if an image compounding method is not dependent on the content of the images (such as method 700) or is static, weight masks may be pre-computed and stored in a memory of the image compounding system. Executing image compounding methods based on pre-computed weight masks may be processed faster and more efficiently by a processor of the image compounding system. FIG. 7 is a flowchart of an exemplary method 700 of performing image compounding on images acquired by a mixed array, where image compounding utilizes pre-computed weight masks with compounding coefficients.

The method 700 may include steps 601-607 as shown and described with respect to FIG. 6. However, the method 700 may further include retrieving pre-computed weight masks (708). The method 700 may then perform weighted average of non-optical images and optical resonator images to generate combined images (709). The weighted average may include arithmetic averaging, geometric averaging, depth-dependent weighting, region-based weighting, and/or the like. The method 700 may further include filtering the combined images (710) and producing compound images (711).

Figure 8:
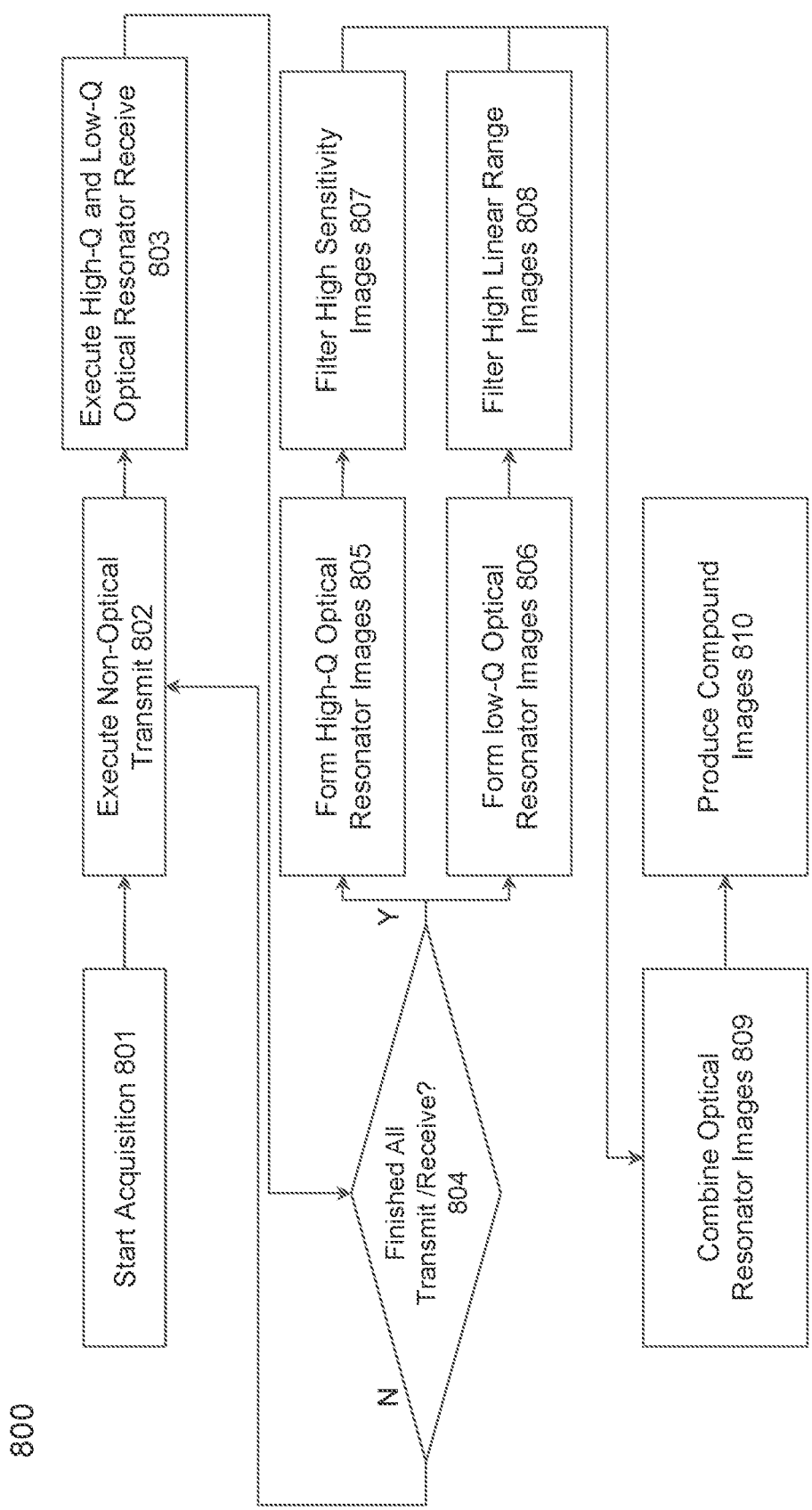
FIG. 8 is a flowchart of an exemplary method of performing image compounding on images acquired by a mixed array.

FIG. 8 is a flowchart of an exemplary method 800 of performing image compounding on images acquired by a mixed array. In some implementations, the method 800 may be performed with the compound imaging system 103 as shown and described with respect to FIG. 3. The method 800 may include initiating image acquisition (801) (e.g., upon receipt of an indication to begin acquisition). The method 800 may further include transmitting a non-optical signal (802) followed by receiving a high quality factor (high Q) optical resonator and/or low quality factor (low Q) optical resonator signal (803). The method 800 may iterate 802 and 803 until all transmit steps desired to transmit acoustic signals from all non-optical array elements and all receive steps to receive acoustic echoes from all high Q optical resonator array elements and low Q optical resonator array elements are executed. Once all desired transmitting and receiving have been performed for at least one desired compound image (804), the method 800 may further include generating or forming high Q optical resonator images (805) (also referred to as high sensitivity images) and generating or forming low Q optical resonator images (806) (also referred to as high dynamic range images) using the front end 140 and back end 150 of the compound imaging system 103. The back end 150 may then filter the high Q optical resonator images (807) and filter the low Q optical resonator images (808). The method 800 may include combining the high Q optical resonator images and the low Q optical resonator images (809) (e.g., using a compounding algorithm) and producing the compound images (810). Similar to method 700, in some variations (e.g., if method 800 is not dependent on the content of the images or is static), weight masks may be pre-computed and stored in a memory of the image compounding system 103 for faster processing.

Figure 9:
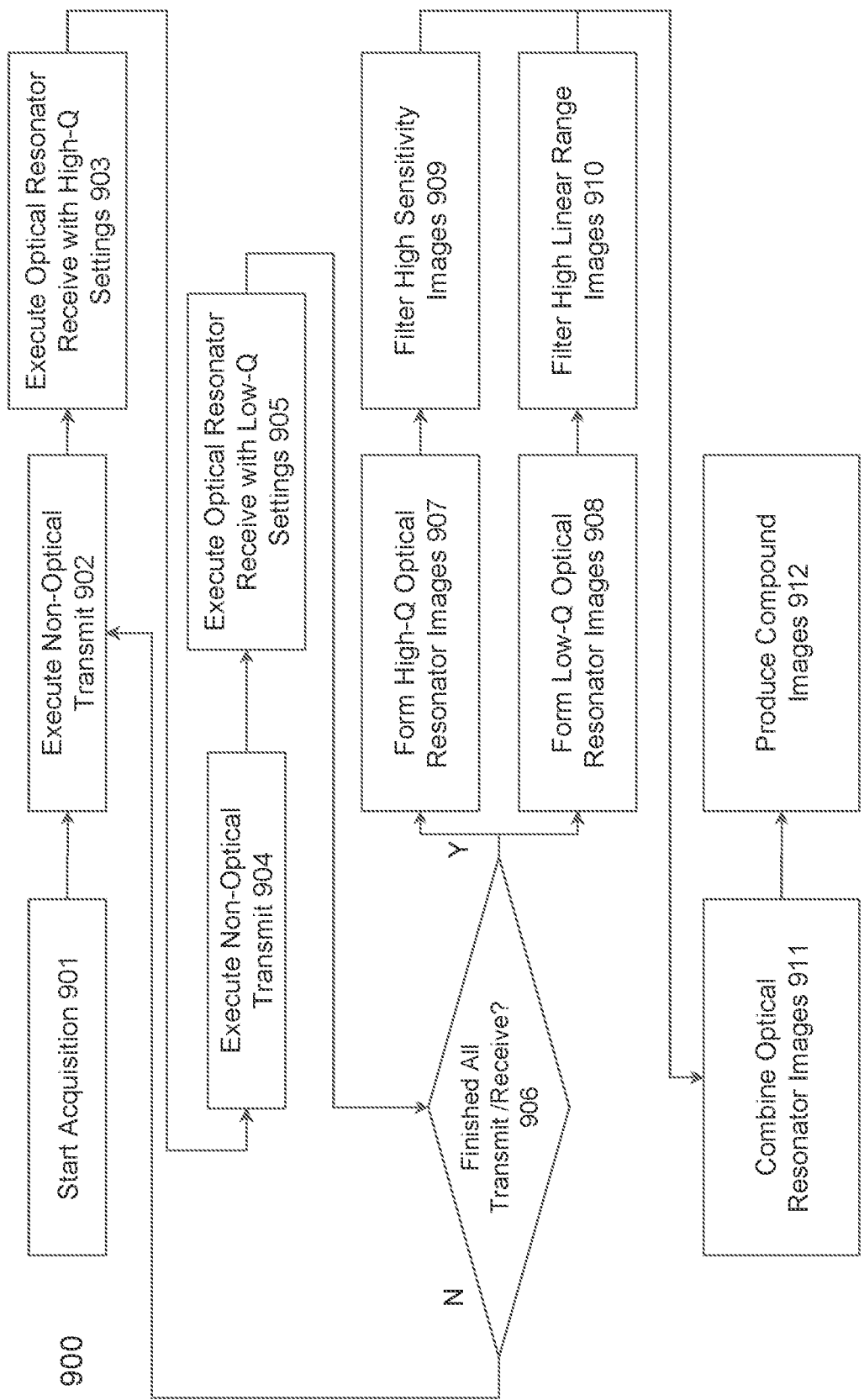
FIG. 9 is a flowchart of an exemplary method of performing image compounding on images acquired by a mixed array.

FIG. 9 is a flowchart of an exemplary method of performing image compounding on images acquired by a mixed array. In some implementations, the method 900 may be performed with the compound imaging system 104 as shown and described with respect to FIG. 4. The method 900 may include initiating image acquisition (901) (e.g., upon receipt of an indication to begin acquisition). The method 900 may further include transmitting a non-optical signal (902) followed by receiving an optical resonator signal from at least one tunable optical resonator signal operating in a high Q mode (903). In some instances, the optical resonators may be operated at the high Q setting by choosing the optical wavelength (of a light source) to match a resonance frequency in which the quality factor of the resonance is high. The method 900 may further include transmitting a non-optical signal (904) followed by receiving an optical resonator signal from at least one tunable optical resonator signal operating in a low Q mode (905). While the flowchart FIG. 9 depicts receiving signals from optical resonators in high Q mode prior to receiving signals from optical resonators in low Q mode, it should be understood that alternatively, signals from optical resonators in low Q mode may be received prior to receiving signals from optical resonators in high Q mode. The method 900 may iterate the 902-905 until all transmit steps desired to transmit acoustic signals from all non-optical array elements and all receive steps to receive acoustic echoes at all Q optical resonator array elements in low Q setting and high Q setting are executed. Once all desired transmitting and receiving has been performed for at least one desired compound image (906), the method 900 may further include generating or forming high Q optical resonator images (907) and generating or forming low Q optical resonator images (908) using the front end 140 and back end 150 of the compound imaging system 104. The back end 150 may then filter the high Q optical resonator images (909) and filter the low Q optical resonator images (910). The method 900 may include combining the high Q optical resonator images and the low Q optical resonator images (911) (e.g., using a compounding algorithm) to produce the compound images (912). Similar to methods 700 and 800, in some variations (e.g., if method 900 is static), weight masks may be pre-computed and stored in a memory of the image compounding system 104 for faster processing.

Figure 10:
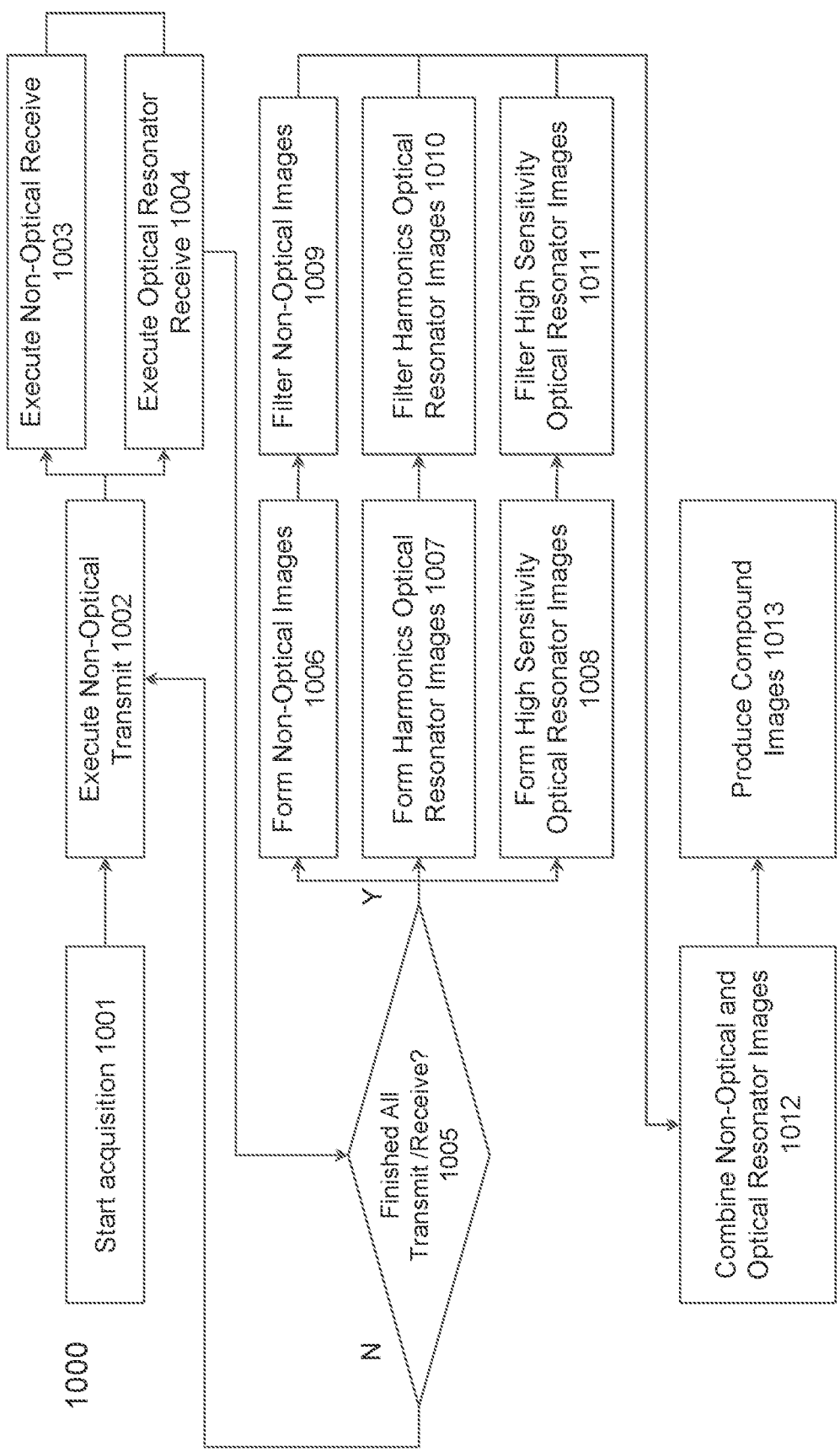
FIG. 10 is a flowchart of an exemplary method of performing image compounding on images acquired by a mixed array.

FIG. 10 is a flowchart of an exemplary method of performing image compounding on images acquired by a mixed array. In some implementations, the method 1000 may be performed with the compound imaging system 105 as shown and described with respect to FIG. 5. The method 1000 may include initiating image acquisition (1001) (e.g., upon receipt of an indication to begin acquisition). The method 1000 may further include transmitting a non-optical signal (1002) followed by receiving a non-optical signal (1003) and receiving an optical resonator signal (1004) (e.g., from a broad bandwidth optical resonator sub-array and/or an ultra-sensitive optical resonator sub-array). The method 1000 may iterate 1002-1004 until all transmit steps desired to transmit acoustic signals from all non-optical array elements and all receive steps to receive acoustic echoes at all non-optical array elements and optical resonator array elements are executed. Once all desired transmitting and receiving steps for at least one desired compound image are performed (1005), the method 1000 may further include generating or forming non-optical images (1006), generating or forming a harmonic optical resonator images (1007), and generating or forming high sensitivity optical resonator images (1008) using the front end 140 and back end 150 of the compound imaging system 105. The back end 150 may then filter the non-optical images (1009), filter the harmonic optical resonator images (1010), and filter the high sensitivity optical resonator images (1011). The filtering of the harmonic optical resonator images (i.e. low Q optical resonator images) may include executing a set of band pass filters and/or a set of one dimensional signal filters to extract the components in the sub-harmonics and/or super-harmonics bands. Subsequently, these filtered signals are used to form harmonics images at each of the selected bands. The method 1000 may include combining the non-optical images, the harmonic optical resonator images, and the high sensitivity optical resonator images 1012 (e.g., using a compounding algorithm) to produce the compound images (1013).

Figure 11B:
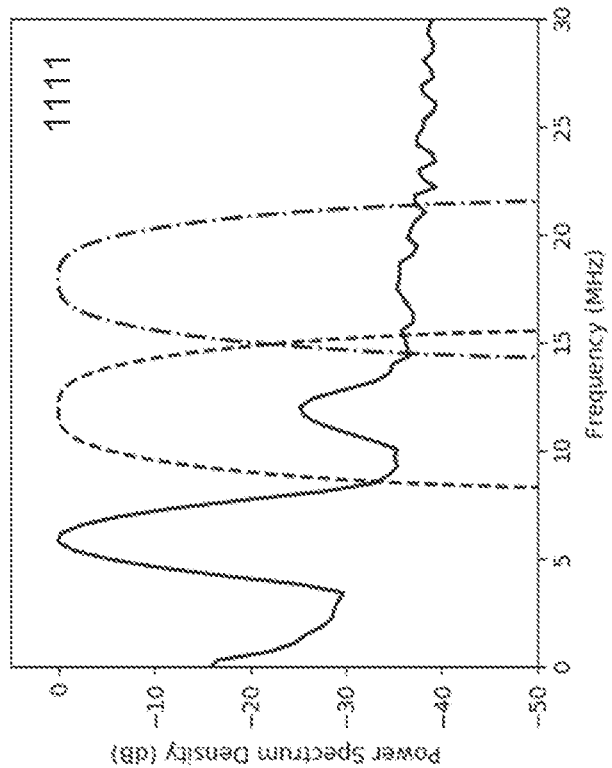
FIGS. 11A-11E show exemplary signals generated by a mixed array and harmonic filtering of the signals.
Figure 11A:
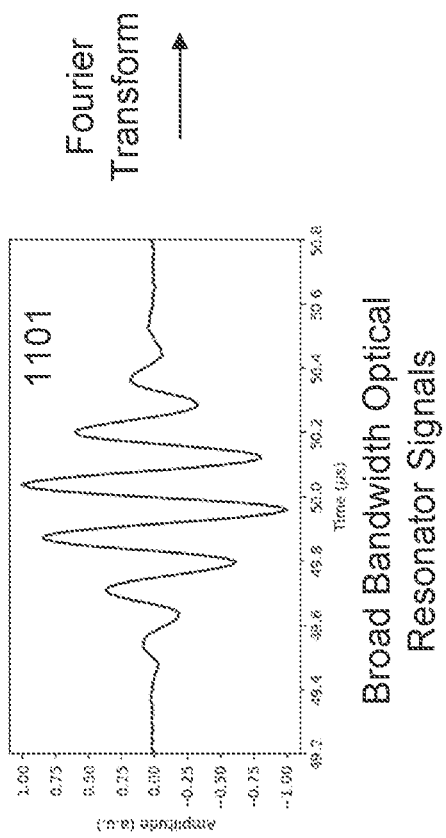

As described above, in forming the harmonic optical resonator images, the optical resonator signals may be processed with a filter bank comprising one or more filters. FIGS. 11A-11E show exemplary signals generated by a mixed array and harmonic filtering of the signals. As shown in FIG. 11A, a first signal 1101 is received by a wide-band optical resonator. By executing a transformation such as, for example, a Fourier Transform the first signal 1101 may be transformed from time domain to the frequency domain 1111. As shown by the solid line in FIG. 11B, the first signal contains mainly the baseband component around 6 MHz with a bandwidth of approximately 87% (or 5.22 MHz). The spectrum of the first signal, however, reveals that a −25 dB second harmonic component and a −35 dB third harmonic component are present in the first signal. The first signal also has a −35 dB additive 1/f pink noise.

Figure 11D:
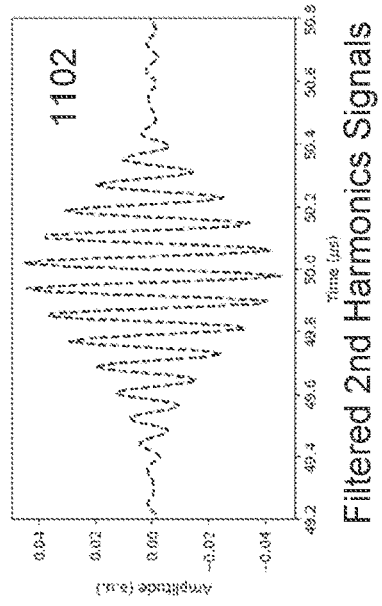
Figure 11E:
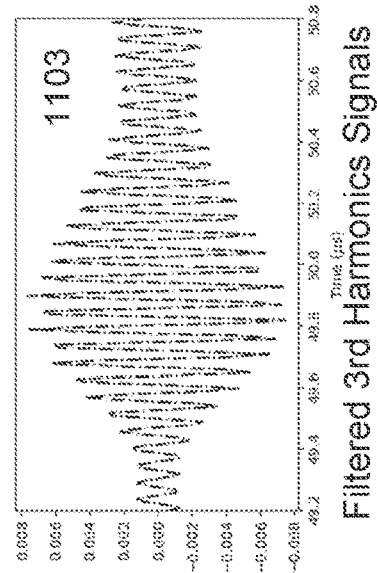
Figure 11C:
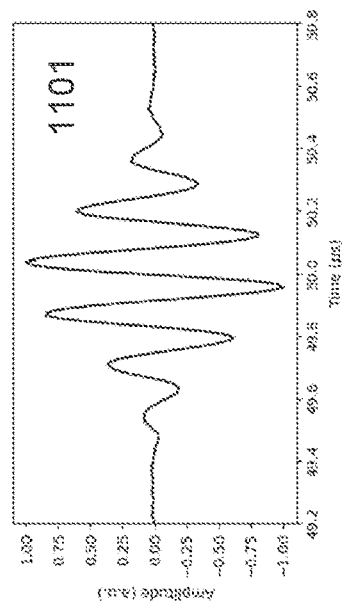

FIGS. 11C-11E illustrates extraction of the harmonic components with suitable filters. For example, a 101 tap Finite Impulse Response (FIR) 2nd harmonic band pass filter may be applied to the first signal 1101 to extract a filtered 2nd harmonic signal 1102 as shown in FIG. 11D. Additionally, a 3rd harmonic band pass filter (the dash-dotted line in the bottom right panel), may be applied to the first signal 1101 to extract a filtered 3rd harmonic signal 1103. In some instances, temporal signals (signals in time domain) may be normalized, and the 2nd and 3rd harmonic signals may be much weaker than the baseband signals. This is because tissue generated super-harmonic signals are usually (e.g., orders of magnitude) lower than the baseband signals. Moreover, higher frequency signals suffer from larger losses in biological tissues. Without a broad bandwidth sensor such as optical resonators described herein, and methods and apparatus for compound imaging based on signals generated by the optical resonators harmonic imaging may be extremely difficult to achieve.

Compounding Algorithms

Exemplary compounding algorithms to combine multiple images based on signals from non-optical array elements and/or optical resonator array elements are described herein. In some instances, n images of m-dimensions (m-D) are combined (through image compounding) to generate a single m-D image computed as the output (n and m being integers). When m is 2, the m-D images are called "images", while when m is 3, they may be referred to as "volumes". Compounding algorithms described may be applied to both images and volumes. Generally, in some variations, compounding algorithms may produce compounding coefficients (e.g., factors) that characterize which or how much of each feature(s) (e.g., pixel intensity) of each separate image (e.g., non-optical image, optical resonator image) may contribute to each compound image. The compounding coefficients may be described in a weighting mask that may be applied to an image to extract the desired features for contribution to a compound image.

In some variations, the compounding algorithm may be or include arithmetic averaging. The idea behind arithmetic averaging for compound imaging based on signals received from a mixed array is to combine n input images into one output image with direct pixel-by-pixel arithmetic averaging of the pixel values:

$$I_f[x] = \frac{1}{n}\sum_{j=1}^{n} I_j[x]$$

where, x is the m-D coordinate of a pixel. The n input images may include non-optical array elements and/or optical resonators. In some instances, the compound images may undergo one or more scaling operations before being displayed on a fixed dynamic range display device or stored in a database with a predefined dynamic range.

In some variations, the compounding algorithm may be or include geometric averaging. Similar to the arithmetic averaging method described above, the geometric averaging method is also a pixel wise (pixel-by-pixel) method performed by:

$$I_f[x] = \left(\prod_{j=1}^{n} I_j[x]\right)^{1/n}$$

Figure 12:
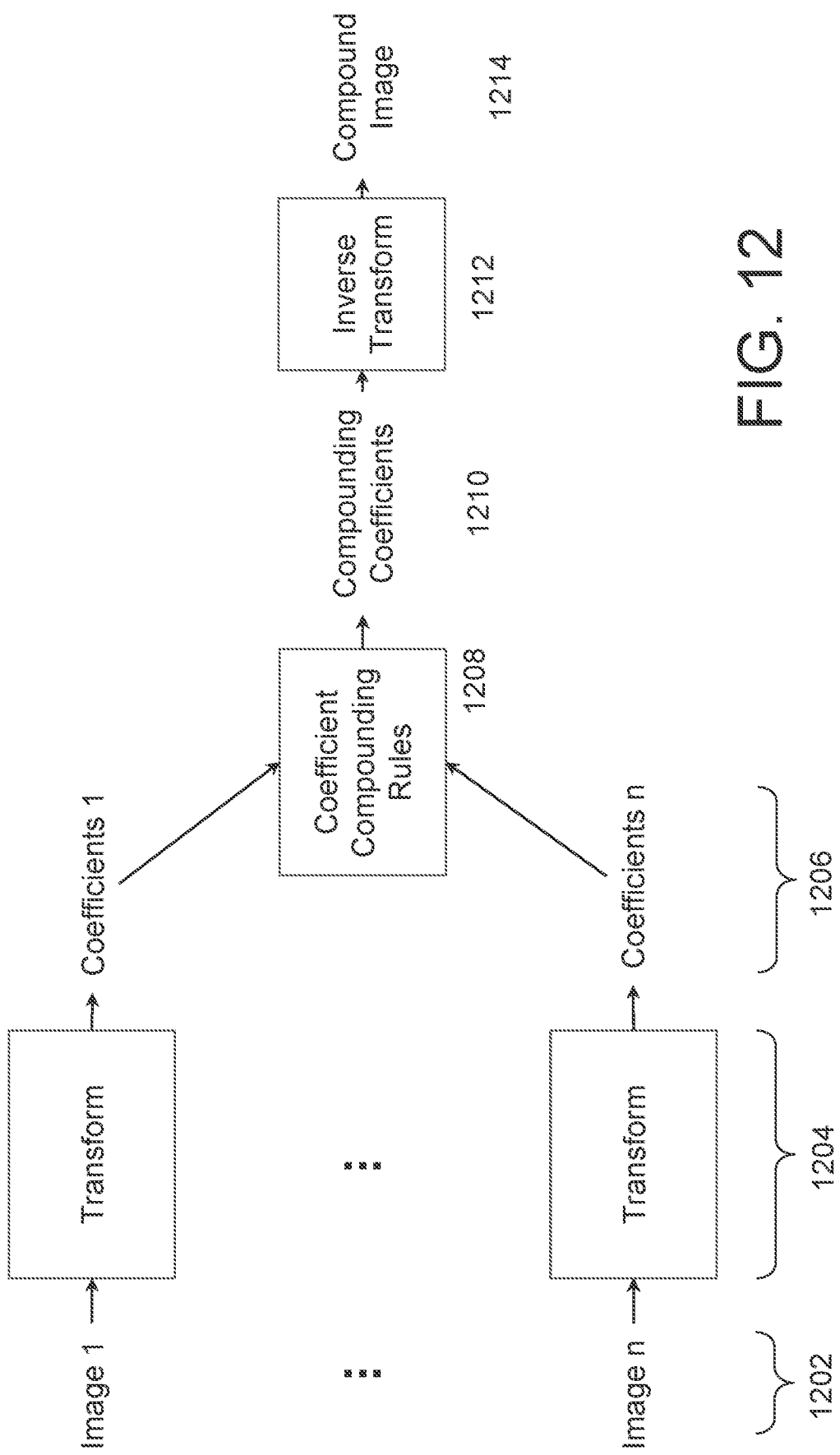
FIG. 12 shows a method of performing image compounding on images acquired by a mixed array.

In some variations, the compounding algorithm may be or include transform domain compounding. This is a class of compounding methods that relies on transforming the input images into a transform domain that supports 1-to-1 forward and backward transformations. The 1-to-1 transformation may include, for example, a Fourier Transform, a Discrete Wavelet Transform (DWT), a Discrete Cosine Transform (DCT), a Wave Atom Transform, and/or the like. After transformation, a set of heuristic-based or learned rules may be applied to obtain the compounding coefficients in the transform domain. Then, the inverse transformation may be performed to convert the compounding coefficients back to the image domain. An example of this process is shown in FIG. 12. The input images 1202 (non-optical images and/or optical resonator images) may undergo a transformation 1204 and coefficients 1206 may be generated. Coefficient compounding rules 1208 may be applied to these coefficients to generate compounding coefficients 1210 in the transform domain. The compounding coefficients may then be inverse transformed 1212 to convert the compounding coefficients to the image domain for use in generating the compound image 1214.

In some variations, transform domain compounding may use transformation that are suitable for multi-scale analysis of images, such as DWT. Under the context of DWT, an illustrative example of coefficient compounding rules includes:

For the smallest scale among multiple scales, take a minimum coefficient among coefficients of all images (e.g., non-optical images, high Q optical image, low Q optical image, and/or the like). This rule assumes that smallest scale contains mainly noises and thus should be minimized.

For the largest scale among the multiple scales, take an average of coefficients for all input images. This rule assumes the largest scale describes the general shape of the object and should be consistent among the input images.

For all other scales (other than the smallest scale and the largest scale) among the multiple scales, take the maximum of coefficients among all input images. This rule assumes that all other scales represent certain details of the target and different input images may be best in representing one or more aspects. By taking the maximum, all details may be preserved.

However, if the DWT method is being applied to the method 1000 as shown and described with respect to FIG. 10, larger weights can be assigned to the smaller scale coefficients of the super-harmonic images and the larger scale coefficients of the non-optical images.

Additionally or alternatively, a set of coefficient compounding rules (e.g., rules that may be learned, such as through a suitable machine learning algorithm) may be pre-defined for different ultrasound frequencies (e.g., as a lookup table, as a function of ultrasound frequency, etc.). For example, a first compounding coefficient (or a first range of compounding coefficients) may be associated with images generated using a high ultrasound frequency (or range of high ultrasound frequencies), and a second compounding coefficient (or a second range of compounding coefficients) may be associated with images generated using a low ultrasound frequency (or range of low ultrasound frequencies). Generally, in some variations, because higher ultrasound frequencies attenuate more in far field imaging, compounding coefficients may be lower with increasing imaging depth such that images generated using a high ultrasound frequency are given less weight in producing the compounding images.

Figure 13:
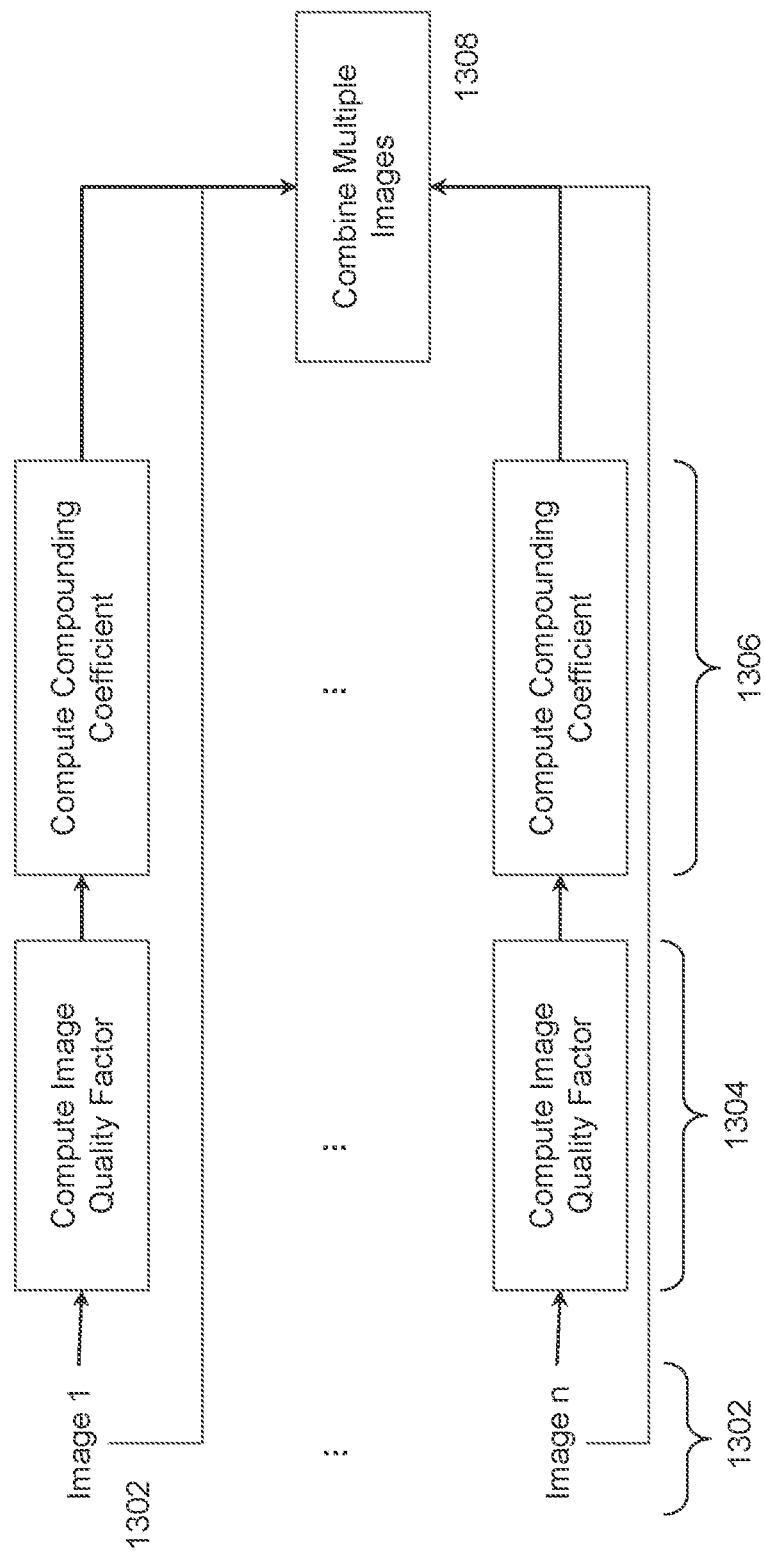
FIG. 13 shows a method of performing image compounding on images acquired by a mixed array.

In some variations, the compounding algorithm may be or include Image Quality Factor (IQF) based compounding, as shown in FIG. 13. An image quality factor (IQF) may be defined as a quantitative measure of image quality, and may be expressed or otherwise characterized at least in part by an image quality factor map for an image. There are various IQFs developed for various purposes and applications. For example, each of and/or any combinations of signal to noise ratio (SNR), entropy, detail resolution, contrast resolution, and penetration depth may be used as an IQF. Different IQFs enhance different aspects of ultrasound images. In some instances, one or more IQFs 1304 may be extracted from input images 1302. The IQFs 1304 are then converted into compounding coefficients 1306. The compound image $I_f(x)$ 1308 may be calculated by a weighted sum of the input images $I_j(x)$, $$I_f(x) = \left(\sum_{j=1}^{n} W_j[x] \cdot I_j[x]\right) \Big/ \left(\sum_{j=1}^{n} W_j[x]\right)$$

where x represents the 2D or 3D coordinates, $W_j[x]$ is a weighting coefficient map for the j-th input image. The input images may be optical resonator image and/or non-optical images depending on the compound imaging system as shown and described with respect to FIGS. 1-5.

In some variations, the compounding algorithm may be or include local entropy weighted compounding. The local entropy weighted compounding combines the input images by assigning weights to each pixel of each input image based on the information content in the neighborhood. This may be done by computing the entropy of a region surrounding each pixel of each input image. The local entropy of the pixel at the coordinate x in the j-th image may be calculated by:

$$H_{x,j} = -p_{x,j} \cdot \log_2(p_{x,j})$$

where $p_{x,j}$ is the histogram of the neighborhood of the pixel at the coordinate x in the j-th image. For this particular pixel, the unnormalized weight may be assigned as:

$$W_j[x] = 100^{H_{x,j}}$$

Many functions that convert $H_{x,j}$ to a non-negative value may be used in lieu of this particular example. The compound image may be expressed as:

$$I_f[x] = \left(\sum_{j=1}^{n} W_j[x] \cdot I_j[x]\right) \Big/ \left(\sum_{j=1}^{n} W_j[x]\right)$$

In some variations, the compounding algorithm may be or include fast image content weighted compounding. As an approximation of local entropy-based weighting, a faster, linear filtering-based algorithm may also be used. Instead of computing local entropy of the input images, which could be computationally expensive, $W_j[x]$ is computed by applying a Difference of Gaussian (DoG) filter to the j-th image. To generate the compound image the same formula as local entropy weighted compounding may be used.

In some variations, the compounding algorithm may be or include depth dependent weighted compounding. If the input images have well defined characteristics that are depth dependent, a predefined depth-dependent weighting may be useful. The depth dependent weighted compounding may be particularly helpful when the optical resonator sub-array includes or is operated as an ultra-sensitive optical resonator (e.g., as shown in FIGS. 3 and 4), as some input images can have better quality in the shallower regions and the other images can have better quality in the deeper regions. Many depth weighting functions may be used, including but not limited to linear and gamma functions.

In some variations, the compounding algorithm may be or include saturation masking. When some input images are prone to signal saturation (e.g., images produced by high Q optical resonators) or other type of nonlinearity due to excessive signal amplitude, a saturation masking step may be introduced to these input images before they are put through the compounding methods. Signal saturation may be detected by comparing the moving average of a beamformed image with a predefined threshold. When saturation is detected, the saturated pixels of the input image under examination may be assigned a zero or close to zero weight so that its contribution to the compound image will be small and other input image or images, which are not saturated, will dominate.

Although image compounding methods and systems for mixed arrays have been described in the context of ultrasound imaging, in some variations, the image compounding methods and systems may be used in applications other than ultrasound imaging. For example, in some instances, the image compounding methods and systems may be used in computed tomography, magnetic resonance imaging, metrology, signal processing, particle physics, remote sensing, aerospace applications, and/or the like. The image compounding methods disclosed here can also be applied to combine images generated with different imaging modalities to form a fused image. For example, an ultrasound image, a CT image, and an MRI image of the same region of a patient can be fused together to show more diagnostic information.

Although, in some variations described above, the tunable optical resonators are described as operating at a low quality factor (low Q) operation mode or a high quality factor (high Q) operation mode, in general, the tunable optical resonators may be operated in multiple operation modes (e.g., 3 operation modes, 10 operation modes, 100 operation modes). For example, the tunable optical resonators may be operated at a low Q operation mode to generate a first image having high linear range, a high Q operation mode to generate a second image having high sensitivity, and a medium quality factor operation mode to generate a third image having a balance between sensitivity and linear range. The back end of the image compounding system 100 may be configured to combine the first image, the second image, and the third image to generate a compound image that is better (e.g., resolution, depth, contrast, quality factor, and/or the like) compared to each of the first image, the second image, or the third image.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method of imaging comprising:
receiving a first signal from one or more array elements of a first type in a mixed transducer array;
receiving a second signal from one or more array elements of a second type in the mixed transducer array, wherein at least one of the first type and the second type is an optical sensor, wherein the second type is a broad bandwidth optical sensor;
receiving a third signal from one or more array elements of a third type in the mixed transducer array;
generating a first image from the first signal, a second image from the second signal, a third image from the third signal; and
combining the first image, the second image, and the third image to generate a compound image.

2. The method of claim 1, wherein the first type and the second type are optical resonators with different characteristics.

3. A method of imaging, comprising:
receiving a first signal from one or more array elements of a first type in a mixed transducer array;
receiving a second signal from one or more array elements of a second type in the mixed transducer array, wherein at least one of the first type and the second type is an optical sensor;
generating a first image from the first signal and a second image from the second signal;
determining one or more compounding coefficients for the first image and the second image, comprising:
transforming the first and second images to first and second transform domain images using at least one transformation operator;
determining one or more transform domain compounding coefficients for the first and second transform domain images; and
inverse transforming the one or more transform domain compounding coefficients to determine the one or more compounding coefficients for the first and second images; and
combining the first image and the second image based on the one or more compounding coefficients to generate a compound image, combining the first image and the second image comprising determining a weighted average of the first image and the second image.

4. The method of claim 3, wherein determining one or more transform domain compounding coefficients for the first and second transform domain images comprises applying one or more coefficient compounding rules to the first and second transform domain images.

5. A method of imaging, comprising:
receiving a first signal from one or more array elements of a first type in a mixed transducer array;
receiving a second signal from one or more array elements of a second type in the mixed transducer array, wherein at least one of the first type and the second type is an optical sensor;
generating a first image from the first signal and a second image from the second signal;
determining one or more compounding coefficients for the first image and the second image, comprising:
determining a first image quality factor map for the first image and a second image quality factor map for the second image; and
determining a first compounding coefficient for the first image based on the first image quality factor map, and a second compounding coefficient for the second image based on the second image quality factor map; and
combining the first image and the second image based on the one or more compounding coefficients to generate a compound image, combining the first image and the second image comprising determining a weighted average of the first image and the second image.

6. A method of imaging, comprising:
receiving a first signal from one or more array elements of a first type in a mixed transducer array;
receiving a second signal from one or more array elements of a second type in the mixed transducer array, wherein at least one of the first type and the second type is an optical sensor;
generating a first image from the first signal and a second image from the second signal;
determining one or more compounding coefficients for the first image and the second image, comprising:
determining a local entropy of each pixel in the first image and in the second image; and
determining the one or more compounding coefficients based on the determined local entropies; and combining the first image and the second image based on the one or more compounding coefficients to generate a compound image, combining the first image and the second image comprising determining a weighted average of the first image and the second image.

7. The method of claim 6, wherein determining the one or more compounding coefficients for the first image and the second image further comprises applying a linear filter to each of the first image and the second image.

8. The method of claim 6, wherein determining the one or more compounding coefficients for the first image and the second image further comprises determining the one or more compounding coefficients as a function of imaging depth.

9. A method of imaging, comprising:
receiving a first signal from one or more array elements of a first type in a mixed transducer array;
receiving a second signal from one or more array elements of a second type in the mixed transducer array, wherein at least one of the first type and the second type is an optical sensor;
generating a first image from the first signal and a second image from the second signal; and
combining the first image and the second image to generated a compound image, combining the first image and the second image comprising determining a weighted average of the first image and the second image, determining the weighted average comprising applying a saturation mask that reduces weight of at least a portion of the first image and/or the second image that has exceeded a predetermined saturation threshold.

10. The method of claim 3, wherein at least one of the first image and the second image is a harmonic image.

11. The method of claim 10, wherein the harmonic image is a sub-harmonic image or a super-harmonic image.

12. An apparatus for imaging a target comprising:
a mixed transducer array comprising:
one or more array elements of a first type configured to receive a first signal, the one or more array elements of the first type comprising a non-optical transducer;
one or more array elements of a second type configured to receive a second signal, the one or more array elements of the second type comprising a broad bandwidth optical sensor; and
one or more array elements of a third type configured to receive a third signal, the one or more array elements of the third type comprising an ultra-sensitive optical sensor; and
one or more processors configured to:
generate a first image from the first signal, a second image from the second signal, and a third image from the third image; and
combine the first image, the second image, and the third image to generate a compound image.

13. The apparatus of claim 12, wherein the first type and the second type are optical resonators with different characteristics.

14. The apparatus of claim 12, wherein the non-optical transducer is a piezoelectric transducer, a single crystal material transducer, a piezoelectric micromachined ultrasound transducer (PMUT), or a capacitive micromachined ultrasonic transducer (CMUT).

15. An apparatus for imaging a target, comprising:
a mixed transducer array comprising:
one or more array elements of a first type configured to receive a first signal, the one or more array elements of the first type comprising a non-optical transducer;
one or more array elements of a second type configured to receive a second signal, wherein the one or more array elements of the second type comprising an optical sensor; and
one or more array elements of a third type configured to receive a third signal, the one or more array elements of the third type comprising an ultra-sensitive optical sensor; and
one or more processors configured to:
filter the first signal, the second signal, and/or the third signal using one or more filters;
generate a first image from the first signal, a second image from the second signal, and a third image from the third signal; and
combine the first image, the second image, and the third image to generate a compound image.

16. The apparatus of claim 15, wherein the one or more filters comprise a harmonic band-pass filter.

17. The method of claim 3, wherein determining the one or more compounding coefficients for the first image and the second image further comprises applying a linear filter to each of the first image and the second image.

18. The method of claim 3, wherein determining the one or more compounding coefficients for the first image and the second image further comprises determining the one or more compounding coefficients as a function of imaging depth.

19. The method of claim 5, wherein determining the one or more compounding coefficients for the first image and the second image further comprises applying a linear filter to each of the first image and the second image.

20. The method of claim 5, wherein determining the one or more compounding coefficients for the first image and the second image further comprises determining the one or more compounding coefficients as a function of imaging depth.

21. The method of claim 5, wherein at least one of the first image and the second image is a harmonic image.

22. The method of claim 21, wherein the harmonic image is a sub-harmonic image or a super-harmonic image.

23. The method of claim 6, wherein at least one of the first image and the second image is a harmonic image.

24. The method of claim 23, wherein the harmonic image is a sub-harmonic image or a super-harmonic image.

25. The method of claim 9, wherein at least one of the first image and the second image is a harmonic image.

26. The method of claim 25, wherein the harmonic image is a sub-harmonic image or a super-harmonic image.

27. The method of claim 1, wherein combining the first image and the second image comprises determining an arithmetic or geometric average of the first image and the second image.

* * * * *